US011130746B2

(12) United States Patent
Martin

(10) Patent No.: US 11,130,746 B2
(45) Date of Patent: Sep. 28, 2021

(54) THERAPEUTIC COMPOUNDS

(71) Applicant: C4X Discovery Limited, Manchester (GB)

(72) Inventor: Barrie P. Martin, Manchester (GB)

(73) Assignee: C4X Discovery Limited, Manchester (GB)

( * ) Notice: Subject to any disclaimer, the term of this patent is extended or adjusted under 35 U.S.C. 154(b) by 0 days.

(21) Appl. No.: 16/860,572

(22) Filed: Apr. 28, 2020

(65) Prior Publication Data

US 2020/0255404 A1    Aug. 13, 2020

Related U.S. Application Data

(63) Continuation of application No. 16/073,429, filed as application No. PCT/EP2017/051960 on Jan. 30, 2017, now Pat. No. 10,696,654.

(30) Foreign Application Priority Data

Jan. 29, 2016    (GB) ...................... 1601703

(51) Int. Cl.
C07D 401/14    (2006.01)
(52) U.S. Cl.
CPC .................. *C07D 401/14* (2013.01)
(58) Field of Classification Search
CPC .................................................. C07D 401/14
See application file for complete search history.

(56) References Cited

U.S. PATENT DOCUMENTS

| | | | |
|---|---|---|---|
| 5,968,965 A | 10/1999 | Dinsmore et al. |
| 6,066,738 A | 5/2000 | Dinsmore et al. |
| 6,727,267 B2 | 4/2004 | Jaen et al. |
| 6,861,448 B2 | 3/2005 | Brouillette et al. |
| 6,905,739 B2 | 6/2005 | Cherkaoui et al. |
| 6,953,857 B2 | 10/2005 | Nazare et al. |
| 7,067,665 B2 | 6/2006 | Nazare et al. |
| 7,338,950 B2 | 3/2008 | Kelly et al. |
| 7,468,367 B2 | 12/2008 | Coulton et al. |
| 7,501,538 B2 | 3/2009 | Mjalli et al. |
| 7,544,699 B2 | 6/2009 | Mjalli et al. |
| 7,872,133 B2 | 1/2011 | Ohmoto et al. |
| 8,039,674 B2 | 10/2011 | Habashita et al. |
| 8,653,305 B2 | 2/2014 | Habashita et al. |
| 8,987,271 B2 | 3/2015 | Cardone et al. |
| 10,011,595 B2 | 7/2018 | Kim et al. |
| 10,611,760 B2 | 4/2020 | Blaney et al. |
| 10,696,654 B2 | 6/2020 | Martin |
| 2002/0198195 A1 | 12/2002 | Nazare et al. |
| 2004/0266732 A1 | 12/2004 | Galvez et al. |
| 2005/0080087 A1 | 4/2005 | Pendri et al. |
| 2008/0262046 A1 | 10/2008 | Coleman et al. |
| 2011/0212975 A1 | 9/2011 | Kao et al. |
| 2011/0263662 A1 | 10/2011 | Aissaoui et al. |
| 2012/0316147 A1 | 12/2012 | Bissantz et al. |
| 2017/0291897 A1 | 10/2017 | Blaney et al. |
| 2020/0270247 A1* | 8/2020 | Blaney .................... A61P 25/20 |

FOREIGN PATENT DOCUMENTS

| | | |
|---|---|---|
| EP | 1349847 A1 | 10/2003 |
| EP | 1456203 A1 | 9/2004 |
| EP | 1637521 A1 | 3/2006 |
| EP | 1698335 A1 | 9/2006 |
| EP | 1760071 A1 | 3/2007 |
| EP | 1979341 A1 | 10/2008 |
| EP | 2462138 A1 | 6/2012 |
| EP | 2532661 A1 | 12/2012 |
| EP | 2730570 A1 | 5/2014 |
| EP | 2891489 A1 | 7/2015 |
| EP | 2891492 A1 | 7/2015 |
| GB | 240685 A | 10/1925 |
| JP | 2002/326980 A | 11/2002 |
| JP | 2003/012625 A | 1/2003 |
| JP | 2006/526653 A | 11/2006 |
| JP | 2007/537300 A | 12/2007 |
| JP | 2008/533151 A | 8/2008 |
| JP | 2008-239617 A | 10/2008 |
| JP | 2010/534626 A | 11/2010 |
| JP | 2012056871 A | 3/2012 |
| JP | 2013216634 A | 10/2013 |
| WO | WO-97027852 A1 | 8/1997 |
| WO | WO-0147862 A1 | 7/2001 |
| WO | WO-0177091 A2 | 10/2001 |
| WO | WO-2001/91558 A1 | 12/2001 |
| WO | WO-2003/051872 A1 | 6/2003 |
| WO | WO-05014532 A1 | 2/2005 |

(Continued)

OTHER PUBLICATIONS

Benting et al., "Preparation of arylalkylpyrazolecarboxamide derivatives and analogs for use as fungicides," Calpus, (2011).
Boss et al., "Recent Trends in Orexin Research—2010 to 2015," Bioorganic & Medicinal Chemistry Letters, 25:2875-2887 (2015).
Boss, "Orexin Receptor Antagonists—A Patent Review (2010 to Aug. 2014)," Expert Opinion, 24(12):1367-1381 (2014).
Braga et l., "Mild and efficient one-pot synthesis of chiral ß-chalcogen amides via 2-oxazoline ring-opening reaction mediated by indium," Journal of Organometallic Chemistry, 693:3563-3655 (2008).
Cai et al., "Antagonists of the Orexin Receptors," Expert Opinion, 16(5):631-646 (2006).
CAS Registry No. 1115194-20-1 (2009).
Clapp, "Reactions of ethylenimines with ammonia and amines," CAPLUS 1948:15572 (1948).

(Continued)

*Primary Examiner* — Erich A Leeser
(74) *Attorney, Agent, or Firm* — Foley Hoag LLP; David P. Halstead

(57) ABSTRACT

The present invention relates to compounds that are antagonists of the orexin-1 receptor. The compounds have the structural formula (I) defined herein. The present invention also relates to processes for the preparation of these compounds, to pharmaceutical compositions comprising them, and to their use in the treatment of diseases or disorders associated with orexin-1 receptor activity.

7 Claims, No Drawings

(56) References Cited

FOREIGN PATENT DOCUMENTS

| | | |
|---|---|---|
| WO | WO-05014533 A2 | 2/2005 |
| WO | WO-05032493 A2 | 4/2005 |
| WO | WO-2005/090345 A1 | 9/2005 |
| WO | WO-2005/095327 A1 | 10/2005 |
| WO | WO-06038594 A1 | 4/2006 |
| WO | WO-2006/110626 A1 | 10/2006 |
| WO | WO-03006628 A3 | 10/2006 |
| WO | WO-2007/088999 A1 | 8/2007 |
| WO | WO-2007/126934 A2 | 11/2007 |
| WO | WO-08002671 A2 | 1/2008 |
| WO | WO-2008/061781 A1 | 5/2008 |
| WO | WO-2009/011775 A1 | 1/2009 |
| WO | WO-2009/022311 A2 | 2/2009 |
| WO | WO-2010012795 A1 | 2/2010 |
| WO | WO-2010/086366 A1 | 8/2010 |
| WO | WO-2011/015037 A1 | 2/2011 |
| WO | WO-2011/073316 A1 | 6/2011 |
| WO | WO-2012/021837 A2 | 2/2012 |
| WO | WO-2012/088438 A1 | 6/2012 |
| WO | WO-2013048942 A1 | 4/2013 |
| WO | WO-2013/066833 A1 | 5/2013 |
| WO | WO-2013076230 A1 | 5/2013 |
| WO | WO-2013158928 A2 | 10/2013 |
| WO | WO-2014/044738 A1 | 3/2014 |
| WO | WO-2014/159591 A1 | 10/2014 |
| WO | WO-2015/188073 A1 | 12/2015 |
| WO | WO-2016/034882 A1 | 3/2016 |
| WO | WO-2016/100161 A1 | 6/2016 |

OTHER PUBLICATIONS

Coleman et al., "Discovery of [(2R,5R0-5-{[(5-Flouropyridin-2-yl)oxy]methyl}-2-methylpiperidin-1-yl][5-methyl-2-(pyrimidin-2-yl)phenyl]methanone (MK-6096): A Dual Orexin Receptor Antagonist with Potent Sleep-Promoting Properties," ChemMedChem, 7(3):415-424 (2012).

Coleman et al., "Discovery of Dual Orexin Receptor Antagonists (DORAs) for the Treatment of Insomnia," Current Topics in Medicinal Chemistry, 11:696-725 (2011).

Coleman et al., "Orexin Receptor Antagonists: A Review of Promising Compounds Patented Since 2006," Expert Opinion, 20(3):307-324 (2010).

Imperatore et al., "Effects of the Radical Savenger AVS on Behavioral and BBB Changes After Experimental Subarachnoid Hemorrhage," Life Sciences, 66(9): 779-790 (2000).

International Search Report and Written Opinion for International Application No. PCT/EP2017/051960 dated Mar. 8, 2017.

International Search Report and Written Opinion for International Application No. PCT/GB2015/052546 dated Oct. 29, 2015.

Lebold et al., "Selective Orexin Receptor Antagonists," Bioorganic & Medicinal Chemistry Letters, 23:4761-4769 (2013).

Malherbe et al., "Mapping the Binding Pocket of Dual Antagonist almorexant to Human Orexin 1 and Orexin 2 Receptors: Comparison with the Selective OX1 Antagonist SB-674042 and the Selective OX2 Antagonist N-Ethyl-2[(6-methoxy-pyridin-3-yl)-(toluene-2-sufonyl)-amino]-N-pyridin-3-ylmethyl-acetamide (EMPA)," Mol. Pharmacol., 78:81-93 (2010).

McManus et al., "Coupling of bulky, electron-deficient partners in aryl amination in the preparation of tridentate bis(oxazoline) ligands for asymmetric catalysis," J Org Chem, 67:8566-8573 (2002).

Roecker et al., "Orexin Receptor Antagonists: Medicinal Chemistry and Therapeutic Potential," Current Topics in Medicinal Chemistry, 8:977-987 (2008).

U.K. Search Report for Application No. GB1601703.0 dated Nov. 9, 2016.

United Kingdom Search Report for United Kingdom Application No. GB 1415569.1 dated May 8, 2015.

Written Opinion issued by the Intellectual Property Office of Singapore in corresponding Application No. 11201701715P, dated Nov. 20, 2017.

Zhang et al., "Direct borylation of primary C—H bonds in functionalized molecules by palladium catalysis," Angew Chem Int Et, 53:3899-3903 (2014).

* cited by examiner

THERAPEUTIC COMPOUNDS

RELATED APPLICATIONS

This application is a continuation of U.S. patent application Ser. No. 16/073,429, filed Jul. 27, 2018, which is the National Stage of International Patent Application No. PCT/EP2017/051960, filed Jan. 30, 2017, which claims the benefit of United Kingdom Patent Application No. GB 1601703.0, filed Jan. 29, 2016.

INTRODUCTION

The present invention relates to therapeutic compounds. More specifically, the present invention relates to compounds that are inhibitors of the orexin-1 receptor. The present invention also relates to processes for the preparation of these compounds, to pharmaceutical compositions comprising them, and to their use in the treatment of diseases or disorders associated with orexin-1 receptor activity.

BACKGROUND OF THE INVENTION

The neuropeptides Orexin-A (OxA) and Orexin-B (OxB) (also known as Hypocretin-1 and Hypocretin-2) originate from the same prepro-peptide, which is expressed exclusively in the hypothalamus (1). Cleavage of the prepro-peptide (prepro-orexin) yields OxA a 33 amino acid polypeptide which is extensively post-translationally modified (C-terminal amidation, N—terminally cyclised with a pyroglutamyl residue). OxA shares a 46% sequence identity with OxB which is a 28 amino acid, C-terminally amidated linear polypeptide which likely forms a helical secondary structure (3).

The fully functional mature peptide neurotransmitters act as agonists on the orexin-1 ($OX_1$) and orexin-2 ($OX_2$) 7-transmembrane G-protein coupled receptors (also known as HCRTR1 and HCRTR2) that, like the orexin neuropeptides, share a high sequence homology across species (2, 6). $OX_1$ binds both OxA and OxB, albeit, with differential affinity (OxA has >10-fold higher affinity than OxB). On the contrary $OX_2$, which shares a 64% sequence identity with $OX_1$, binds both polypeptides with nearly equivalent affinity (2). The primary G-protein mediated mechanism through which both receptors act is $G_{q/11}$ activation of phospholipase C catalysing the liberation of inositol-1,4,5-triphosphate ($IP_3$), which in turn acts on $IP_3$ receptors to release calcium from intracellular stores. $OX_2$ has also been reported to modulate cAMP levels via activation of $G_s$ and $G_i$ and $OX_1$ appears capable of signalling through $G_{i/o}$ to also modulate cAMP levels (5, 8). The high degree of sequence similarity in the peptides and receptors across species translates into similar in vitro pharmacology (7).

The hypothalamus, where orexin is predominately expressed, regulates a broad array of physiological and behavioural activities. Orexin expression in this brain structure has been mapped immunohistochemically to only a very restricted number of neurons that reside specifically in the perifornical (50%), lateral and dorsomedial areas (4). The projection fields of these neurons have been identified in numerous brain regions, including the cortex, thalamus, hypothalamus, brainstem, and spinal cord, but not the cerebellum (9). This extensive coverage of the brain suggests that the orexin ligand/receptor system is implicated directly or indirectly in the regulation of multiple brain functions. Notably, knockout experiments in mice suggested that the orexin system is a key regulator of behavioural arousal, sleep and wakefulness. Indeed, the observed phenotype in orexin knockout mice was very similar to that of narcolepsy in humans (10, 11). Narcolepsy in humans is a chronic and disabling disorder characterized by excessive sleepiness during the day, fragmented sleep and cataplexy. Studies in dogs have linked the cause of the disorder to the disruption of the $OX_2$ gene or a loss of orexin peptide expression (12). Further supporting evidence that in particular the disruption of $OX_2$ function and or the absence of mature OxB ligand are associated with narcolepsy came from studies in knockout mice (17). Subsequent clinical studies comparing the levels of OxA in the cerebrospinal fluid of narcoleptic patients to normal individuals confirmed that the disruption of the orexin system shows a causal relationship with the occurrence of narcolepsy in humans (13). Additional studies in unusual early onset human narcolepsy resulted in the identification of a mutation in the orexin gene that further strengthened the link between narcolepsy and the orexin system in humans (14). More recently, clinical data demonstrating the pharmacological relevance of the orexins in CNS disorders has emerged. Most notably, clinical trials with small molecule dual $OX_1$ and $OX_2$ antagonists (DORAs) such as BELSOMRA® (Suvorexant), have clearly demonstrated the potential utility of such agents in treating sleep disorders (15, 16, 18). These data together with the pre-clinical evidence presented above clearly implicate $OX_2$ in sleep regulation.

The differential brain expression of $OX_1$ and $OX_2$ coupled with the diversity of neuro-biological effects attributed to the orexins strongly suggests drugs modulating $OX_1$ or $OX_2$ will elicit different biological effects. To this end, recent reports linking the $OX_1$/OxA system specifically to feeding and behavioural disorders are important.

Given that prepro-orexin mRNA levels are mainly found in the lateral and posterior hypothalamus, areas of the brain classically implicated in the regulation of food intake and energy balance/body weight, a link between the orexin system and feeding behaviour is not unexpected (19). The role of the $OX_1$/OxA system in such functions has been strengthened by a series of pre-clinical studies. Thus intracerebroventricular (i.c.v.) administration of OxA (20) has been shown to induce feeding and specific anti-orexin antibodies dose-dependently suppress food intake (21). In particular, the latter study indicates that orexin receptor antagonists should have a beneficial effect on orexin stimulated feeding. This hypothesis is supported by independent in vivo studies, which clearly identify $OX_1$ as the dominant receptor of the orexin system in the regulation of food intake and energy balance. Thus, experiments conducted with selective $OX_1$ and $OX_2$ receptor antagonists have shown that $OX_1$ selective compounds alter food intake and energy balance in circumstances of concurrent exposure to stress (22, 23). The dominant effect of the $OX_1$ on regulating feeding behaviour and energy balance is further supported by observations which show that $OX_1$ expression is selectively up-regulated in response to fasting, whereas those of $OX_2$ are unaffected (24). Finally, studies with an $OX_1$ specific antibody strongly suggests that a selective $OX_1$ antagonist should suppress food intake and thus have potential therapeutic utility for the treatment of feeding related disorders such as binge eating or obesity.

Elevated $OX_1$ levels have also been associated with psychiatric conditions including schizophrenia, anxiety and mood disorders, panic attacks, reward seeking behaviours and addiction (25, 26, 27). Studies with selective $OX_1$ antagonists (SB334867, SB408124) clearly demonstrated a beneficial effect in a clinically relevant animal model of panic thus implying that OX₁ antagonist could provide a novel therapeutic approach for the treatment of panic disorders (27).

Indirect evidence for the involvement of the orexin system in reward seeking behaviour comes from studies which show that orexinergic neurons project to reward associated brain regions such as the nucleus accumbens and ventral tegmental area (28). Direct experimental evidence comes from studies involving the intracerebroventricular (icv) infusion of orexin, which led to a dose-dependent reinstatement of cocaine seeking. The work by Boutrel et al. also links stress pathways to the effect of orexin on addiction and reward (29). Notably, stress is considered a prominent stimulus for relapse in abstinent addicts (31). The link between stress, addiction and orexin was further strengthened by pharmacological studies in a foot-shock model. These showed activation of orexin neurons in specific areas of the posterior and dorsomedial hypothalamus, which are particularly associated with stress but not the lateral hypothalamus, which has a strong link to reward (32). Moreover orexin as a mediator of stress-induced reinstatement of addictive behaviour was also shown for alcohol seeking (30). Importantly the effects of stress induced reinstatement of alcohol and cocaine seeking in animal models can be attenuated with the selective $OX_1$ antagonist SB334867 supporting the therapeutic use of $OX_1$ selective antagonists in these conditions (29, 30).

Finally the Orexin/$OX_1$ pathway has been implicated in nicotine self-administration (33, 34) and re-instatement of nicotine seeking (35, 36). Such data suggest that $OX_1$ antagonists could find utility as smoking cessation therapies.

Taken together the orexin system, and in particular the $OX_1$ pathway, may be considered a target for the treatment of reward seeking behaviours, addiction and related disorders.

WO2003/051872 discloses certain heterocyclic-substituted ethylene diamine derivatives that act as antagonists of orexin-1 ($OX_1$) and orexin-2 ($OX_2$) receptors.

There is, however, a need for compounds that are potent inhibitors of orexin-1 ($OX_1$) activity and which show selectivity for inhibiting orexin-1 ($OX_1$) receptors over orexin-2 ($OX_2$) receptors. This profile would provide effective therapeutic benefit for the treatment of addictive disorders in the absence of activity on the sleep-wake cycle. There is also a need for compounds that exhibit increased residency times at the orexin-1 ($OX_1$) receptor, and in particular, compounds that possess increased residency times at the orexin-1 ($OX_1$) receptor relative to their residency times at the orexin-2 ($OX_2$) receptor. Increasing evidence suggests that the time molecules reside at their cellular target can provide an important indicator of their clinical performance (37) and it is potentially advantageous when developing antagonists of G protein coupled receptors to identify compounds which exhibit slow dissociation from the receptor (38). Furthermore, this increased residence time at the receptor may provide extended duration of action in the clinical setting. Prolonged Orexin-1 antagonist receptor blockade in the absence of prolonged blockade of the Orexin-2 receptor therefore represents a new and potentially powerful approach for the treatment of addictive disorders.

In addition, there is a need for compounds that have one or more favourable pharmaceutical properties (e.g. favourable solubility, high metabolic stability, low propensity for drug-drug interactions, low propensity for off-target pharmacological activity, sufficient pharmacokinetic profiles, good oral bioavailability, high therapeutic index, lack of genotoxicity) that render them suitable for further development as candidate drugs. More specifically, for the treatment of CNS disorders such as the disorders described herein, there is a need for compounds that have favourable blood-brain barrier penetration and compounds that achieve significant Orexin-1 receptor occupancy in the brain following oral administration. Compounds that demonstrate this level of significant target engagement in the brain would be effected to show significant efficacy in Orexin-1 receptor mediated CNS disorders.

SUMMARY OF THE INVENTION

In one aspect, the present invention provides a compound, or a pharmaceutically acceptable salt or solvate thereof as defined herein.

In another aspect, the present invention provides a pharmaceutical composition comprising a compound of the invention as defined herein, or a pharmaceutically acceptable salt or solvate thereof, and one or more pharmaceutically acceptable excipients.

In another aspect, the present invention relates to a compound of the invention as defined herein, or a pharmaceutically acceptable salt or solvate thereof, or a pharmaceutical composition as defined herein, for use in therapy.

In another aspect, the present invention relates to a compound of the invention as defined herein, or a pharmaceutically acceptable salt or solvate thereof, or a pharmaceutical composition as defined herein, for use in the treatment of diseases or conditions in which orexin-1 ($OX_1$) activity is implicated.

In another aspect, the present invention relates to the use of a compound of the invention as defined herein, or a pharmaceutically acceptable salt or solvate thereof, in the manufacture of a medicament for use in the treatment of diseases or conditions in which orexin-1 ($OX_1$) activity is implicated.

In another aspect, the present invention relates to a method of treating a disease or condition in which orexin-1 ($OX_1$) activity is implicated, said method comprising administering to a subject in need of such treatment a therapeutically effective amount of a compound of the invention as defined herein, or a pharmaceutically acceptable salt or solvate thereof, or a pharmaceutical composition as defined herein.

Examples of conditions in which orexin-1 ($OX_1$) activity is implicated include behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides a compound, or a pharmaceutically acceptable salt or solvate thereof, or a pharmaceutical composition as defined herein, for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides the use of a compound, or a pharmaceutically acceptable salt or solvate thereof, in the manufacture of a medicament for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides a method of treating behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety), said method comprising administering to a subject in need of such treatment a therapeutically effective amount of a compound, or a pharmaceutically acceptable salt or solvate thereof, or a pharmaceutical composition as defined herein.

In another aspect, the present invention provides a compound, or a pharmaceutically acceptable salt or solvate thereof, or a pharmaceutical composition as defined herein, for use in the production of an orexin-1 inhibitory effect.

In another aspect, the present invention provides the use of a compound, or a pharmaceutically acceptable salt or solvate thereof, in the manufacture of a medicament for use in the production of an orexin-1 inhibitory effect.

In another aspect, the present invention provides a method of producing an orexin-1 inhibitory effect in vitro, said method comprising administering an effective amount of a compound, or a pharmaceutically acceptable salt or solvate thereof.

In another aspect, the present invention provides a method of producing an orexin-1 inhibitory effect in vivo, said method comprising administering an effective amount of a compound, or a pharmaceutically acceptable salt or solvate thereof.

In another aspect, the present invention provides a method of inhibiting orexin-1 ($OX_1$) in vitro or in vivo, said method comprising contacting a cell with an effective amount of a compound as defined herein, or a pharmaceutically acceptable salt or solvate thereof.

The present invention further provides a method of synthesising a compound, or a pharmaceutically acceptable salt or solvate thereof, as defined herein.

In another aspect, the present invention provides a compound, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods set out herein.

Preferred, suitable, and optional features of any one particular aspect of the present invention are also preferred, suitable, and optional features of any other aspect.

Compounds of the Invention

In a first aspect, the present invention provides a compound of which is selected from:

N,6-dimethyl-3-(2H—1,2,3-triazol-2-yl)—N—[(2S)—1-{[5-(trifluoro methyl)pyrazin-2-yl]amino}propan-2-yl]pyridine-2-carboxamide;

N,6-dimethyl-3-(2H—1,2,3-triazol-2-yl)—N—[(2S)—1-{[5-(trifluoro methyl)pyrimidin-2-yl]amino}propan-2-yl]pyridine-2-carboxamide;

or a pharmaceutically acceptable salt or solvate thereof.

These compounds have the general structural formula I shown below:

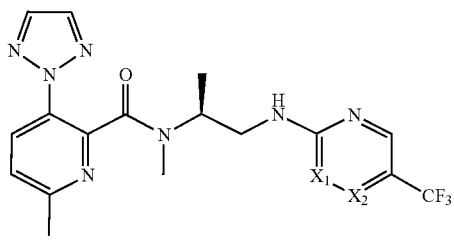

I wherein $X_1$ is —CH— and $X_2$ is —N— or $X_1$ is —N— and $X_2$ is —CH—; or a pharmaceutically acceptable salt or solvate thereof.

In an embodiment, $X_1$ is —CH— and $X_2$ is —N—, i.e. the compound is:

N,6-dimethyl-3-(2H—1,2,3-triazol-2-yl)—N—[(2S)—1-{[5-(trifluoro methyl)pyrazin-2-yl]amino}propan-2-yl]pyridine-2-carboxamide; or a pharmaceutically acceptable salt or solvate thereof.

In an embodiment, $X_1$ is —N— and $X_2$ is —CH—, i.e. the compound is:

N,6-dimethyl-3-(2H—1,2,3-triazol-2-yl)—N—[(2S)—1-{[5-(trifluoro methyl)pyrimidin-2-yl]amino}propan-2-yl] pyridine-2-carboxamide; or a pharmaceutically acceptable salt or solvate thereof.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R— and S—sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)— or (S)—stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. It is to be understood that the present invention encompasses all optical, diastereoisomers and geometric isomers and mixtures thereof that possess orexin-1 inhibitory activity.

The present invention also encompasses compounds of the invention as defined herein which comprise one or more isotopic substitutions. For example, H may be in any isotopic form, including $^1$H, $^2$H (D) and $^3$H (T); C may be in any isotopic form including $^{12}$C, $^{13}$C, and $^{14}$C; and O may be in any isotopic form, including $^{16}$O and $^{18}$O; and the like.

It is also to be understood that certain compounds of the invention may exist in solvated as well as unsolvated forms such as, for example, hydrated forms. It is to be understood that the invention encompasses all such solvated forms that possess orexin-1 inhibitory activity.

It is also to be understood that certain compounds of the invention may exhibit polymorphism, and that the invention encompasses all such forms that possess orexin-1 inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention.

Compounds of the invention containing an amine function may also form N—oxides. A reference herein to a compound of the invention that contains an amine function also includes the N—oxide. Where a compound contains several amine functions, one or more than one nitrogen atom may be oxidised to form an N—oxide. Particular examples of N—oxides are the N—oxides of a tertiary amine or a nitrogen atom of a nitrogen-containing heterocycle. N—Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N—oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the invention as defined hereinbefore when made available by organic synthesis and when made available within the human or animal body by way of cleavage of a pro-drug thereof. Accordingly, the present invention includes those compounds of the invention that are produced by organic synthetic means and also such compounds that are produced in the human or animal body by way of metabolism of a precursor compound, that is a compound of the invention may be a synthetically-produced compound or a metabolically-produced compound.

A suitable pharmaceutically acceptable pro-drug of a compound of the invention is one that is based on reasonable medical judgement as being suitable for administration to the human or animal body without undesirable pharmacological activities and without undue toxicity.

Various forms of pro-drug have been described, for example in the following documents:
- a) *Methods in Enzymology*, Vol. 42, p. 309-396, edited by K. Widder, et al. (Academic Press, 1985);
- b) Design of Pro-drugs, edited by H. Bundgaard, (Elsevier, 1985);
- c) A Textbook of Drug Design and Development, edited by Krogsgaard-Larsen and H. Bundgaard, Chapter 5 "Design and Application of Pro-drugs", by H. Bundgaard p. 113-191 (1991);
- d) H. Bundgaard, *Advanced Drug Delivery Reviews*, 8, 1-38 (1992);
- e) H. Bundgaard, et al., *Journal of Pharmaceutical Sciences*, 77, 285 (1988);
- f) N. Kakeya, et al., *Chem. Pharm. Bull.*, 32, 692 (1984);
- g) T. Higuchi and V. Stella, "Pro-Drugs as Novel Delivery Systems", A.C.S. Symposium Series, Volume 14; and
- h) E. Roche (editor), "Bioreversible Carriers in Drug Design", Pergamon Press, 1987.

The in vivo effects of a compound of the invention may be exerted in part by one or more metabolites that are formed within the human or animal body after administration of a compound of the invention. As stated hereinbefore, the in vivo effects of a compound of the invention may also be exerted by way of metabolism of a precursor compound (a pro-drug).

It shall also be appreciated that compounds of the invention may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated that are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject such as 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3 \cdot OEt_2$. A suitable alternative protecting group for a primary amino group is, for example, a phthaloyl group that may be removed by treatment with an alkylamine, for example dimethylaminopropylamine, or with hydrazine.

The person skilled in the art will recognise that the compounds of the invention may be prepared, in known manner, in a variety of ways. Compounds of the invention can be prepared by the methods given below, by the methods given in the experimental or by analogous methods. The routes described are merely illustrative of some of the methods that can be employed for the synthesis of compounds of the invention and the person skilled in the art will appreciate that the order of the reaction steps is not limited to those described. It will also be appreciated that the assignment of nucleophile and electrophile is not limited to that described herein and in some cases it may be appropriate for the assignment to be reversed. Different approaches to synthetic chemistry strategy are described in "Organic Synthesis: The Disconnection Approach", $2^{nd}$ edition, S. Warren and P. Wyatt (2008).

A compound of the invention, or a pharmaceutically-acceptable salt thereof, may be prepared by reacting an acid, or acid derivative of formula II with an amine of formula III, wherein $X_1$ and $X_2$ are as previously defined in formula I (Scheme A, step i).

A suitably reactive derivative of a carboxylic acid of formula II is, for example: an acyl halide formed by the reaction of the acid and an inorganic acid chloride such as thionyl chloride; a mixed anhydride, formed by the reaction of the acid and a chloroformate such as isobutyl chloroformate; an ester, formed by reaction with an alcohol in the presence of acid or base; an activated ester, formed by the reaction of the acid with a phenol such as pentafluorophenyl trifluoroacetate or with an alcohol such as N—hydroxybenzotriazole; or the product of the reaction of the acid and an amide-coupling agent such as dicyclohexylcarbodiimide. Where a carboxylic acid of formula II is converted to an ester, for example by the reaction of an acyl chloride with an organic alcohol, such as methanol, this may be reacted with an amine of formula III in the presence of an organometallic activating agent, for example a Grignard reagent such as isopropylmagnesium bromide. Typically, a carboxylic acid of formula II and an amine of formula III, in a suitable solvent, such as DMF in the presence of a non-nucleophilic base, such as DIPEA, are treated with an amide-coupling agent, such as HATU.

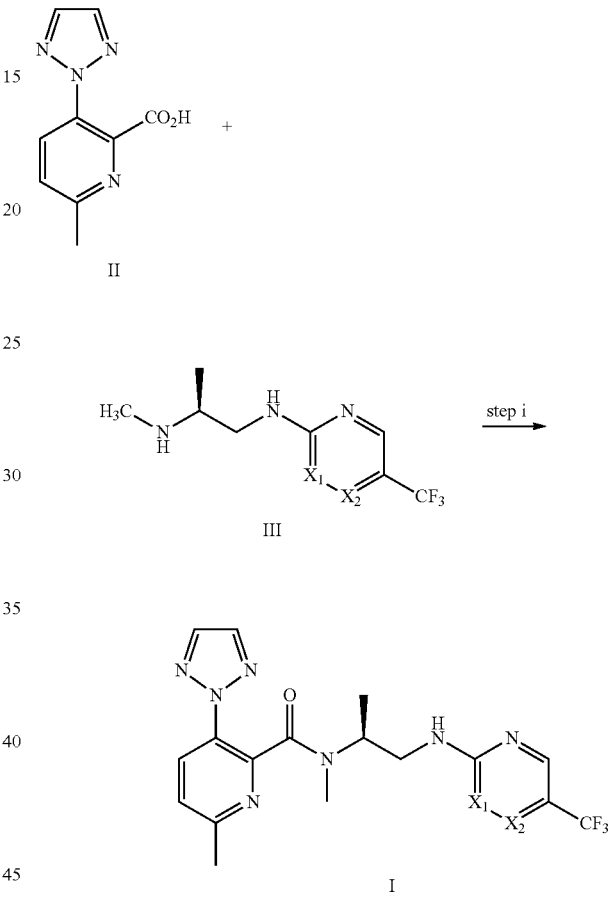

Scheme A

Compounds of formula II may be commercially available or prepared by techniques known, or apparent to, those skilled in the art. Compounds of formula II may be prepared by: acid or base catalysed hydrolysis of an ester, an amide or a nitrile, such as the hydrolysis of a methyl ester with sodium hydroxide; transition metal catalysed oxidation of an aldehyde or alcohol; treatment of an organolithium or Grignard reagent with carbon dioxide; transition metal catalysed carbonylation of an aryl halide in the presence of water. Transition metal catalysed carbonylation of an aryl halide in the presence of an amine of formula III may form a compound of formula I directly.

It will be appreciated by those skilled in the art that compounds of formula I and formula III, wherein $X_1$ and $X_2$ are as previously defined in formula I, may be prepared by incorporating suitable protecting group and route selection strategies into the general synthetic chemistry methodology described in Scheme B, wherein $X_1$ and $X_2$ are as previously defined in formula I and Y is either: H;

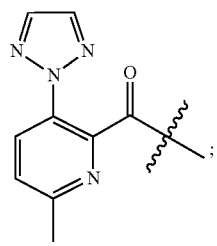 [SMILES: *C(=O)c1nc(C)ccc1-n1nccn1]

or an amine protecting group such as benzyl, 3,4-dimethoxybenzyl p-methoxybenzyl, carbobenzyloxy, tert-butyloxycarbonyl, 9-fluorenylmethyloxycarbonyl, acetyl, benzoyl, p-methoxyphenyl, tosyl, nosyl or trifluoroacetyl.

A compound of formula IV, or a pharmaceutically-acceptable salt thereof, wherein $X_1$ and $X_2$ are as previously defined in formula I, may be prepared by reacting an amine of formula V with a compound of formula ZAr, wherein Ar is

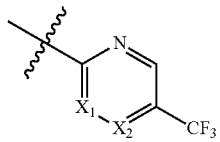

and $X_1$ and $X_2$ are as previously defined in formula I, and Z is a substituent amenable to transition-metal catalysed amination chemistry (Scheme B, step ii). A compound of formula ZAr, wherein Z is a halide such as bromide or chloride, a boronic acid or boronate ester, or an activated alcohol such as a triflate, may be converted to a compound of formula IV by reaction with an amine of formula V in the presence of a transition metal catalyst such as [1,1'-bis(diphenylphosphino)ferrocene]-dichloropalladium(II) or $Pd_2(dba)_3$ in the presence of a base such as potassium carbonate or sodium tert-butoxide and a suitable ligand such as triphenylphosphine or 4,5-Bis(diphenylphosphino)-9,9-dimethylxanthene. Typically the reaction is carried out in toluene, at relux, using $Pd_2(dba)_3$ as a catalyst in the presence of BINAP and sodium tert-butoxide.

Alternatively, a compound of formula IV may be prepared by reacting an amine of formula V with a compound of formula ZAr, wherein Ar is

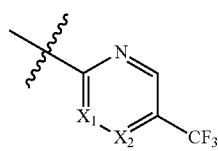

and $X_1$ and $X_2$ are as previously defined in formula I, and Z is a leaving group such as a halide, for example iodide or bromide, or an activated alcohol, for example tosylate or mesylate, in the presence of a non-nucleophilic base such as DBU, sodium tert-butoxide, potassium carbonate, a tertiary amine for example DIPEA, or a heterocyclic base for example pyridine (Scheme B, step ii). Typically the reaction is carried out using DIPEA, as a base, in NMP at 130° C.

A compound of formula IV, or a pharmaceutically-acceptable salt thereof, wherein $X_1$ and $X_2$ are as previously defined in formula I, may be prepared by reacting an amine of formula $H_2NAr$, wherein Ar is

and $X_1$ and $X_2$ are as previously defined in formula I, with an aldehyde of formula VI (Scheme B, step iii). A compound of formula IV may be prepared by reductive amination of compounds of formula VI with an amine of formula $H_2NAr$ in the presence of a suitable reducing agent such as sodium cyanoborohydride, $NaBH(OAc)_3$ or sodium borohydride, in a polar solvent such as methanol, ethanol, THF, DCE or DCM either alone or in combination with an acid such as AcOH. Typically the reaction is carried out using $NaBH(OAc)_3$ in DCE at ambient temperature.

An amine of formula V may be prepared by reductive amination as previously described for Scheme B step iii, between an aldehyde of formula VI and an amine, amine equivalent or suitably protected amine (Scheme B, step iv).

Scheme B

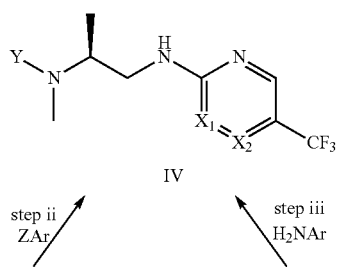

IV step ii    step iii
ZAr       $H_2NAr$

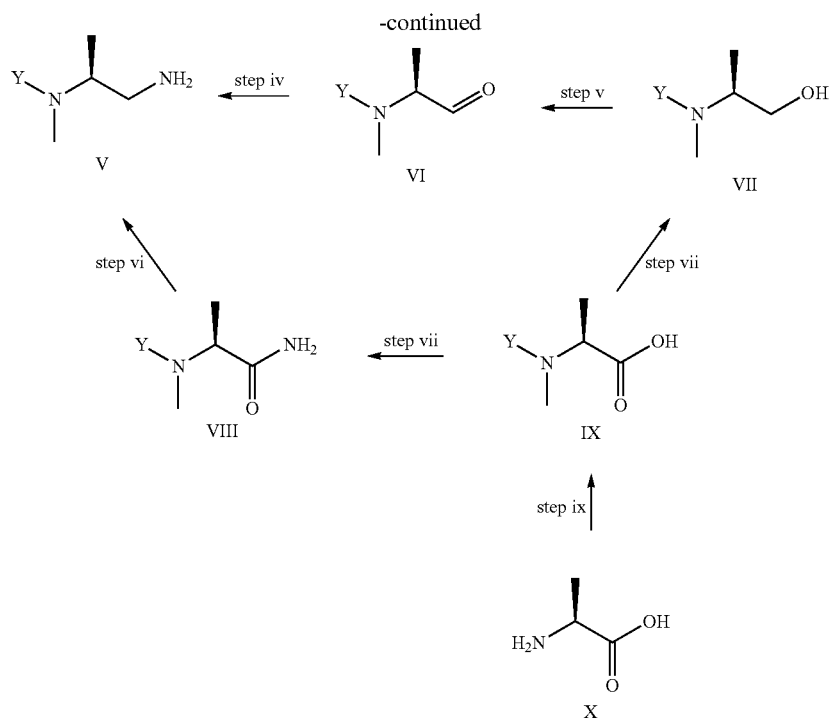

The person skilled in the art will recognise that aldehydes of formula VI can be prepared in a variety of ways. Typically aldehydes of formula VI are prepared by the oxidation of an alcohol of formula VII in DCM using Dess-Martin's Periodinane and NaHCO$_3$ (Scheme B, step v).

Compounds of formula V may also be prepared by reduction of an amide of formula VIII with a hydride reagent such as LiAlH$_4$ or by catalytic hydrogenation (Scheme B, step vi). Typically the reaction is carried out in THF or diethyl ether using LiAlH$_4$ at 0° C. The person skilled in the art will recognise that the preparation of amines of formula V is not limited to the methods described herein and can be achieved in known manner, in a variety of ways.

The person skilled in the art will recognise that alcohols of formula VII can be prepared in a variety of known ways. For example, alcohols of formula VII may be prepared by reduction of carbonyl containing compounds such as aldehydes, carboxylic acids or carboxylic acid equivalents, such as a carboxylic esters, of formula IX (Scheme B, step vii) with a suitable reducing agent such as sodium borohydride, LiAlH$_4$, diisobutyl aluminium hydride or LiBH$_4$. Typically alcohols of formula VII are prepared by reduction of carboxylic ester equivalents of carboxylic acids of formula IX using LiBH$_4$ in THF at ambient temperature. It will be appreciated by a person skilled in the art that a carboxylic ester equivalent of a carboxylic acid of formula IX can be prepared in a variety of known ways.

Compounds of formula IX may be prepared from a suitably protected/activated derivative of an amino acid of formula X (Scheme B, step ix). It will be appreciated by those skilled in the art that conversion of an amino acid of formula X to a compound of formula IX via a synthetic strategy of protection/activation may require multiple reaction steps, and can be achieved in a variety of ways of known manner. For example, compounds of formula IX can be prepared by: conversion of an amino acid of formula X to an activated amide such as a trifluoroacetamide by reaction with trifluoroacetic anhydride, followed by deprotonation with a base such as sodium hydride, alkylation with an alkyl halide of formula CH$_3$Z, wherein Z is a leaving group such as a halide or an activated alcohol, for example methyl iodide, and hydrolysis with a suitable base such as sodium hydroxide; benzylic protection by reaction of an amino acid of formula X with a suitable aldehyde or aldehyde equivalent such as benzaldehyde, followed by reductive amination with an suitable aldehyde or aldehyde equivalent, such as formaldehyde or paraformaldehyde, followed by catalytic hydrogenation with a transition metal catalyst such as palladium under an atmosphere of hydrogen; conversion of an amino acid of formula X to a carbamate by reaction with an anhydride or acid chloride such as with di-tert-butyl dicarbonate, followed by reduction with a metal-hydride such as LiAlH$_4$.

Natural and non-natural amino acids of formula X and their derivatives are either commercially available or may be prepared by methods known to those skilled in the art. For reviews of the synthesis of amino acids, see (a) C. Najera and J. M. Sansano, Chem. Rev., 2007, 107, 4584; (b) R. M. Williams and J. A. Hendrix, Chem. Rev., 1992, 92, 889; (c) R. O. Duthaler, Tetrahedron, 1994, 50, 1539.

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The compounds of the invention are selective inhibitors of orexin-1 activity. As a consequence, they are potentially useful therapeutic agents for the treatment of diseases or conditions in which orexin-1 receptor activity is implicated.

Thus, in one aspect, the present invention relates to a compound of the invention as defined herein, or a pharmaceutically acceptable salt or solvate thereof, or a pharmaceutical composition as defined herein, for use in therapy.

In another aspect, the present invention relates to a compound of the invention as defined herein, or a pharmaceutically acceptable salt or solvate thereof, or a pharmaceutical composition as defined herein, for use in the treatment of diseases or conditions in which orexin-1 ($OX_1$) activity is implicated.

In another aspect, the present invention relates to the use of a compound of the invention as defined herein, or a pharmaceutically acceptable salt or solvate thereof, in the manufacture of a medicament for use in the treatment of diseases or conditions in which orexin-1 ($OX_1$) activity is implicated.

In another aspect, the present invention relates to a method of treating a disease or condition in which orexin-1 ($OX_1$) activity is implicated, said method comprising administering to a subject in need of such treatment a therapeutically effective amount of a compound of the invention as defined herein, or a pharmaceutically acceptable salt or solvate thereof, or a pharmaceutical composition as defined herein.

Examples of particular diseases or conditions that the compounds of formula (I) and their pharmaceutically acceptable salts may be used to treat include, but are not limited to, any one of the following: schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichlofiilomania or body dysmorphic disorder); mood disorders (e.g., depressive disorders, major depressive disorders, bipolar disorders including bipolar I and II, bipolar mania, bipolar depression);

addiction including substance dependence (e.g. cocaine, opiates, cannabis or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease).

In particular, the compounds of the invention (including pharmaceutically acceptable salts) may be used in the treatment of the positive symptoms of schizophrenia, schizophreniform disorder or schizoaffective disorder (e.g. voices or hallucinations), cognitive disorders (such as dementia and impaired learning), anxiety disorders (such as post-traumatic stress disorder or panic disorders), or addiction.

The invention also provides a compound of formula I as defined herein for use in the treatment of at least one symptom or condition associated with the treatment of any one of the following: schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dysmorphic disorder); mood disorders (e.g., depressive disorders, major depressive disorders, bipolar disorders including bipolar I and II, bipolar mania, bipolar depression); addiction including substance dependence (e.g. cocaine, opiates, cannabis or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease) which comprises administering to a patient in need thereof a therapeutically effective amount of a compound of formula (I) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

Further particular examples of conditions in which orexin-1 ($OX_1$) activity is implicated include behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides a compound, or a pharmaceutically acceptable salt or solvate thereof, or a pharmaceutical composition as defined herein, for use in the treatment of schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dysmorphic disorder); mood disorders (e.g., depressive disorders, major depressive disorders, bipolar disorders including bipolar I and II, bipolar mania, bipolar depression); addiction including substance dependence (e.g. cocaine, opiates, cannabis or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease).

In another aspect, the present invention provides a compound, or a pharmaceutically acceptable salt or solvate thereof, or a pharmaceutical composition as defined herein, for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides the use of a compound, or a pharmaceutically acceptable salt or solvate thereof, in the manufacture of a medicament for use in the treatment of schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dysmorphic disorder); mood disorders (e.g., depressive disorders, major depressive disorders, bipolar disorders including bipolar I and II, bipolar mania, bipolar depression); addiction including substance dependence (e.g. cocaine, opiates, cannabis or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease).

In another aspect, the present invention provides the use of a compound, or a pharmaceutically acceptable salt or solvate thereof, in the manufacture of a medicament for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety).

In another aspect, the present invention provides a method of treating schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dysmorphic disorder); mood disorders (e.g., depressive disorders, major depressive disorders, bipolar disorders including bipolar I and II, bipolar mania, bipolar depression); addiction including substance dependence (e.g. cocaine, opiates, cannabis or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease), said method comprising administering to a subject in need of such treatment a therapeutically effective amount of a compound, or a pharmaceutically acceptable salt or solvate thereof, or a pharmaceutical composition as defined herein.

In another aspect, the present invention provides a method of treating behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety), said method comprising administering to a subject in need of such treatment a therapeutically effective amount of a compound, or a pharmaceutically acceptable salt or solvate thereof, or a pharmaceutical composition as defined herein.

In another aspect, the present invention provides a compound, or a pharmaceutically acceptable salt or solvate thereof, or a pharmaceutical composition as defined herein, for use in the production of an orexin-1 inhibitory effect.

In another aspect, the present invention provides the use of a compound, or a pharmaceutically acceptable salt or solvate thereof, in the manufacture of a medicament for use in the production of an orexin-1 inhibitory effect.

In another aspect, the present invention provides a method of producing an orexin-1 inhibitory effect in vitro, said method comprising administering an effective amount of a compound, or a pharmaceutically acceptable salt or solvate thereof.

In another aspect, the present invention provides a method of producing an orexin-1 inhibitory effect in vivo, said method comprising administering an effective amount of a compound, or a pharmaceutically acceptable salt or solvate thereof.

In another aspect, the present invention provides a method of inhibiting orexin-1 ($OX_1$) in vitro and/or in vivo, said method comprising contacting a cell with an effective amount of a compound as defined herein, or a pharmaceutically acceptable salt or solvate thereof.

Routes of Administration

The compounds of the invention or pharmaceutical composition comprising the active compound may be administered to a subject by any convenient route of administration, whether systemically/peripherally or topically (i.e. at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The compounds of the invention may be administered alone as a monotherapy or may administered in combination with one or more additional therapeutic agents. The selection of the one or more additional therapeutic agents will of course vary depending on the disease or condition to be treated and its severity.

It is commonplace to use combination therapies to treat certain medical conditions.

Therefore, the treatment defined hereinbefore may be applied as a sole therapy or may involve, in addition to the compound of the invention, treatment with one or more additional therapeutic agents.

Such conjoint/combination treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to a particular aspect of the invention there is provided a combination suitable for use in the treatment of a disease or condition in which orexin-1 receptor activity is implicated, comprising a compound of the invention as defined hereinbefore, or a pharmaceutically acceptable salt or solvate thereof, and another therapeutic agent.

According to this aspect of the invention there is provided a combination suitable for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction and/or anxiety), the combination comprising a compound of the invention as defined hereinbefore, or a pharmaceutically acceptable salt or solvate thereof, and one or more additional therapeutic agents.

In a further aspect of the invention there is provided a compound of the invention or a pharmaceutically acceptable salt or solvate thereof, in combination with one or more additional therapeutic agents.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with one or more additional therapeutic agents in association with a pharmaceutically acceptable diluent or carrier.

According to a particular aspect of the invention there is provided a combination suitable for use in the treatment of schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichotillomania or body dysmorphic disorder); mood disorders (e.g., depressive disorders, major depressive disorders, bipolar disorders including bipolar I and II, bipolar mania, bipolar depression); addiction including substance dependence (e.g. cocaine, opiates, cannabis or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); osteoporosis and neurodegenerative disorders (e.g. Parkinson's or Alzheimer's disease), the combination comprising a compound of the invention as defined hereinbefore, or a pharmaceutically acceptable salt or solvate thereof, and another therapeutic agent.

According to a particular aspect of the invention there is provided a combination suitable for use in the treatment of behavioural arousal, eating disorders (e.g. binge eating, obesity), psychiatric conditions (e.g. schizophrenia, anxiety, mood disorders, reward seeking behaviours, alcohol or drug (e.g. nicotine) addiction, panic disorders (such as panic attacks) and/or anxiety) comprising a compound of the invention as defined hereinbefore, or a pharmaceutically acceptable salt or solvate thereof, and another therapeutic agent.

Examples of other therapeutic agents that may be used as part of a combination therapy with a compound of the present invention (e.g. as one of two or more active agents as part of double or triple combinations) include, but are not limited to, the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, tianeptine, thionisoxetine, tranylcypromaine, trazodone, trimipramine, venlafaxine, vortioxetine and equivalents and pharmaceutically active isomer(s) and/or metabolite(s) thereof;

(ii) antipsychotics including, for example, amisulpride, aripiprazole, asenapine, benzisoxidil, bifeprunox, brexpiprazole, carbamazepine, cariprazine, clozapine, chlorpromazine, dibenzepin, divalproex, duloxetine, eszopiclone, haloperidol, iloperidone, lamotrigine, loxapine, iurasidone, mesoridazine, olanzapine, paliperidone, perlapine, perphenazine, phenothiazine, phenyibutlypiperidine, pimozide, proclorperazine, quetiapine, risperidone, sertindole, sulpiride, suproclone, suri clone, thioridazine, trifluoperazine, trimetozine, valproate, valproic acid, zopiclone, zotepine, zicronapine, ziprasidone, and equivalents and pharmaceutically active isomer(s) and/or metabolite(s) thereof;

(iii) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazeparn, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uidazepam, and zolazepam; and equivalents and pharmaceutically active isomer(s) and/or metabolite(s) thereof;

(iv) anticonvulsants including, for example, carbamazepine, valproate, lamotrigine, evetiracetam and gabapentin, and equivalents and pharmaceutically active isomer(s) and/or metabolite(s) thereof;

(v) Alzheimer's therapies including, for example, donepezil, gaiantamine, memantine, rivastigmine, tacrine, and equivalents and pharmaceutically active isomer(s) and/or metabolite(s) thereof;

(vi) Parkinson's therapies including, for example, L-dopa, ropinirole, pramipexole, monoamine oxidase type B (MAO-B) inhibitors such as deprenyl, selegiline and rasagiline, a catechol-O-methylS transferase (COMT) inhibitors such as entacapone or tolcapone, adenosine A-2 inhibitors, dopamine re-uptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(vii) migraine therapies including, for example, aimotriptan, amantadine, botulinum toxin A, bromocriptine, butalbital, cabergoline, dichloralphenazone, dihydroergotamine, eletriptan, frovatriptan, lisuride, naratriptan, pergolide, pramipexole, rizatriptan, ropinirole, sumatriptan, topiramate, zolmitriptan, and zomitriptan, and equivalents and pharmaceutically active isomer(s) and/or metabolite(s) thereof;

(viii) stroke therapies including, for example, abciximab, activase, citicoline, desmoteplase, and equivalents and pharmaceutically active isomer(s) and/or metabolite(s) thereof;

(ix) urinary incontinence therapies including, for example, darafenacin, duloxetine, flavoxate, mirabegron, oxybutynin, propiverine, robalzotan, solifenacin, and tolterodine, and equivalents and pharmaceutically active isomer(s) and/or metabolite(s) thereof;

(x) neuropathic pain therapies including, for example, capsaicin, gabapentin, iiododerm, and pregabalin, and equivalents and pharmaceutically active isomer(s) and/or metabolite(s) thereof;

(xi) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(xii) insomnia therapies including, for example, allobarbital, alonimid, amobarbital, benzoctamine, butabarbital, capuride, chloral, cloperidone, clorethate, dexclamol, ethchlorvynol, eszopiclone, etomidate, glutethimide, halazepam, hydroxyzine, iorediplon, mecloqualone, melatonin, mephobarbital, methaqualone, midaflur, nisobamate, pentobarbital, phenobarbital, propofol, ralmeteon, roletamide, suvorexant, triclofos, secobarbital, zaleplon, and Zolpidem, zopiclone and equivalents and pharmaceutically active isomer(s) and/or metabolite(s) thereof;

(xiii) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;

(xiv) 5HT1B ligands such as, for example, compounds disclosed in WO 99/05134 and WO 02/08212;

(xv) mGluR2 agonists;

(xvi) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;(xvii) chemokine receptor CCR1 inhibitors;

(xviii) delta opioid agonists such as, for example, compounds disclosed in WO 97/23466 and WO 02/094794; and (xiv) osteoporosis therapies such as, for example, bisphosphonates, denosumab, raloxifene, calcitonin, strontium ranelate, HRT, calcium and vitamin D.

(xvv) other agents useful in the treatment of addictive disorders such as buprenorphine, naloxone, metyrapone, naltrexone, nalmefene, ketoconazole, mirtazapine, atomoxetine, gabapentin, muscimol, baclofen, progabide, pregabalin, riluzole, vigabatrin, valproic acid, tiagabine, lamotrigine, phenytoin, carbamazepine, topiramate, a barbiturate, carisoprodol, chloral hydrate, glutethimide, L-theanine, kava, methaqualone, neuroactive steroids, z-drugs, propofol, scullcap, valerian, gamma-butyrolactone, gamma-hydroxybutyric acid, phenibut, deramciclane, hyperforin, gabaculine, phenelzine, valproate, vigabatrin, lemon balm (Melissa officinalis), GABA, L-glutamine, picamilon, and tetanospasmin.

Such combination therapies employ the compounds of this invention within the dosage range described herein and the other pharmaceutically active agent within approved dosage ranges and/or the dosage such as described in the publication reference.

EXAMPLES

Synthesis of Compounds

General Procedures:

Methods for preparing the compounds of this invention are illustrated in the following Examples. Starting materials are made according to procedures known in the art or as illustrated herein, or are available commercially. Commercial reagents were used without further purification. Where no reaction temperature is included, the reaction was performed at ambient temperature which is typically 18-27° C.

Where compounds described in the invention are characterized by ¹H NMR spectroscopy, spectra were recorded on 500 MHz Bruker, 400 MHz Bruker or 400 MHz JEOL instruments. Where no temperature is included the spectra were recorded at ambient temperature. Chemical shift values are expressed in parts per million (ppm). Where NMR spectra are complex due to the presence of interconverting isomers, approximate partial integrations of signals are reported. The following abbreviations are used for the multiplicity of the NMR signals: s=singlet, b=broad, t=triplet, q=quartet, m=multiplet, d=doublet.

Where compounds described in the invention are characterized by LCMS data, retention time and molecular weight are determined using the conditions listed below. In cases where compounds of the invention appear as slowly interconverting stereoisomers, multiple retention times are reported.

Method A: Agilent 1260 LC with MS detection (API electrospray). Column: Agilent Poroshell 120 EC-C18 (2.7 μm, 3.0×50 mm) Conditions: Water+0.1% formic acid [eluent A]; MeCN [eluent B]. Gradient: 5 to 95 to 5% B over 3.5 min.

Method B: Waters ZQ MS with Agilent 1100 HPLC at 210-420 nm (ESI). Column: Phenomenex Gemini—NXC18 (3 μm, 2.0×50 mm). Conditions: 2 mM ammonium bicarbonate, buffered to pH10 [Eluent A]; MeCN [Eluent B]. Gradient: 1 to 100 to 1% B over 3.5 min.

Method C: Waters ZQ MS with Agilent 1100 HPLC at 210-420 nm (ESI). Column: Phenomenex Gemini—NXC18 (3 μm, 2.0×100 mm). Conditions: 2 mM ammonium bicarbonate, buffered to pH10 [Eluent A]; MeCN [Eluent B]. Gradient: 5 to 100 to 5% B over 7 min.

Abbreviations:
DCE Dichloroethane
DCM Dichloromethane
DEAD Diethyl azodicarboxylate
DIPEA N,N—Diisopropylethylamine
DMF N,N—Dimethylformamide
DMSO Dimethylsulfoxide
EtOAc Ethylacetate
HATU N—[(Dimethylamino)-1H—1,2,3-triazolo-[4,5-b]pyridin-1-ylmethylene]—N—methylmethanaminium hexafluorophosphate N—oxide
HBTU N,N,N',N'-Tetramethyl-O—(1H-benzotriazol-1-yl)uraniurn hexafluorophosphate
HCl Hydrogen chloride
HPLC High Performance Liquid Chromatography
hr(s) hour(s)
IPA Isopropyl alcohol
LCMS Liquid Chromatography Mass Spectrometry
LiAlH₄ Lithium aluminium hydride
LiOH Lithium hydroxide
MeCN Acetonitrile
MgSO₄ Magnesium sulfate
min(s) minute(s)
NaBH(OAc)₃ Sodium triacetoxyborohydride
NaHCO₃ Sodium bicarbonate
Na₂SO₄ Sodium sulfate
NMP N—Methylpyrolidinone
NMR Nuclear magnetic resonance
tBME tert-Butyl methyl ether
THF Tetrahydrofuran
TFA Trifluoroacetic acid Preparation of 6-methyl-3-(2H—1,2,3-triazol-2-yl)picolinic acid lithium salt (1:1) (Int 4, Scheme 1)

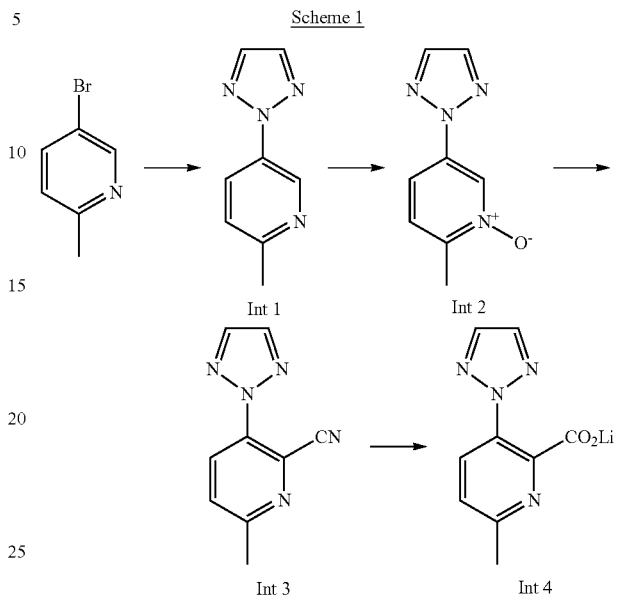

Scheme 1

Preparation of 2-methyl-5-(2H—1,2,3-triazol-2-yl)pyridine (Int 1)

5-Bromo-2-methylpyridine (124 g, 720 mmol), 1H—1,2,3-triazole (210 mL, 3600 mmol), Rac-trans—N,N'-dimethylcyclohexane-1,2-diamine (26.0 g, 183 mmol), copper powder (46 g, 720 mmol) and potassium carbonate (200 g, 720 mmol) were combined in NMP (250 mL). The mixture was heated to 120° C. and stirred for 4 hrs. The mixture was allowed to cool to 50-90° C. and diluted with water (600 mL). The mixture was then added to an agitated mixture of water (1900 mL) and concentrated ammonia solution (124 mL). tBME (600 mL) was added and the mixture was stirred for 0.5 hrs and then filtered washing with tBME (300 mL). The biphasic filtrate was separated. The aqueous was extracted with tBME (2×500 mL) and the organics combined and used directly in the next step.

LCMS (Method A): 1.67 min, 161 [M+H]+

Preparation of 2-methyl-5-(2H—1,2,3-triazol-2-yl)pyridine 1-oxide (Int 2)

To the Int 1 tBME solution was added 3-chloroperbenzoic acid (≤77%, 156 g, 670 mmol) and the mixture was stirred overnight at ambient temperature. The mixture was then heated to 45-50° C. Triethylamine (4 mL) was added and the mixture stirred for 15 mins. The mixture was then subjected to azeotropic drying with additions of tBME. The mixture was then cooled to 10-20° C. and the crude solid product was filtered, washed with tBME (300 mL) and dried. The crude product was stirred in IPA (680 mL) and heated to reflux to cause dissolution. The mixture was then allowed to cool to ambient temperature and stirred overnight. The mixture was then cooled to approximately 5° C. and stirred for 0.5 hrs. The mixture was filtered, washed with cold IPA (95 mL) and tBME (160 mL) and dried to afford the title compound as a solid (62.5 g).

LCMS (Method A): 1.56 min, 177 [M+H]+

Preparation of 6-methyl-3-(2H—1,2,3-triazol-2-yl)picolinonitrile (Int 3)

Trimethylsilyl cyanide (56.3 g, 568 mmol) was added to Int 2 (50.0 g, 284 mmol) in DCM (250 mL) at ambient temperature. The mixture was stirred for 1 hr and then cooled to 10° C. Benzoyl chloride (59.8 g, 425 mmol) was added and the mixture was heated to 40° C. and stirred overnight. The mixture was then poured into saturated aqueous NaHCO₃ (750 mL). Triethylamine (7.5 mL) was added and the mixture stirred at 40° C. overnight. The aqueous phase was separated and extracted with DCM (100 mL). The combined organics were washed with water (200 mL), dried over Na₂SO₄, filtered and concentrated to give the crude product. This material was stirred in hexane (504 mL) and ethyl acetate (56 mL) overnight. The product was filtered, washed with hexane (100 mL) and dried to give the title compound as a solid (48.7 g).

LCMS (Method A): 1.99 min, 186 [M+H]+
Preparation of 6-methyl-3-(2H—1,2,3-triazol-2-yl)picolinic acid lithium salt (1:1) (Int 4)

Lithium hydroxide monohydrate (16.5 g, 393 mmol) in water (130 mL) was added to Int 3 (66.1 g, 357 mmol) in warm IPA (460 mL) and the mixture was heated to 80° C. and stirred overnight. The mixture was then subjected to azeotropic drying with additions of IPA. The resulting suspension was stirred overnight at ambient temperature. The product was filtered, washing with IPA and dried to afford the title compound as a solid (67.8 g).

LCMS (Method A): 1.42 min, 205 [M+H]+
Preparation of N—[(2S)-1-aminopropan-2-yl]—N,6-dimethyl-3-(2H—1,2,3-triazol-2-yl)pyridine-2-carboxamide (Int 11, Scheme 2)

NaBH(OAc)₃ (12 g, 56 mmol) was added and the mixture stirred at ambient temperature for 16 hrs under an atmosphere of nitrogen. The mixture was diluted with DCM (100 mL), quenched with saturated aqueous NaHCO₃ and the phases were separated. The aqueous phase was extracted with DCM. The combined organic phases were washed with water, brine, dried over MgSO₄, filtered and concentrated in vacuo to give the title compound as a colourless oil (3.2 g). The crude product was used without further purification in subsequent reactions.

LCMS (Method B): 1.33 min, 194 [M+H]+
1H NMR (500 MHz, CDCl₃) δ 7.35-7.30 (m, 4H), 7.26 (s, 1H), 3.80 (d, 1H), 3.73 (s, 3H), 3.67 (d, 1H), 3.40 (d, 1H), 1.32 (d, 3H).
Preparation of methyl (2S)-2-[benzyl(methyl)amino]propanoate (Int 7)

To a solution of Int 6 (1.5 g, 6.8 mmol) in DCE (35 mL) was added molecular sieves (1 g), an aqueous solution of formaldehyde (37%; 1.0 mL, 14 mmol) and NaBH(OAc)₃ (3.0 g, 14 mmol) and the mixture was stirred at ambient temperature for 1 hr. The solution was decanted and washed with saturated aqueous NaHCO₃. The organic phase was dried over MgSO₄, filtered and concentrated in vacuo to afford the title compound as a colourless oil (1.3 g). The crude product was used without further purification in subsequent reactions.

Scheme 2

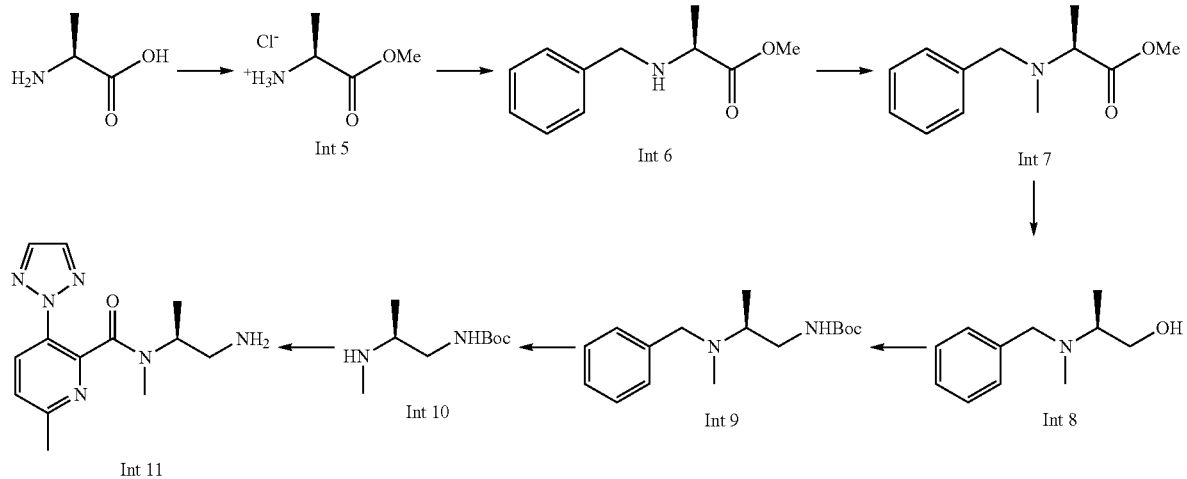

Preparation of (2S)-1-methoxy-1-oxopropan-2-aminium chloride (Int 5)

To a solution of L-alanine (5.0 g, 56 mmol) in methanol (60 mL) at −20° C. was added dropwise thionyl chloride (6.1 mL, 84 mmol) and the mixture was stirred at ambient temperature overnight. The solvent was removed in vacuo. The solid residue was washed with diethyl ether, filtered and dried under vacuum to afford the title compound as a white solid (7.7 g). The crude product was used without further purification in subsequent reactions.

1H NMR (500 MHz, d4-MeOH) δ 4.11 (q, 1H), 3.84 (s, 3H), 1.54 (d, 3H).
Preparation of methyl (2S)-2-(benzylamino)-3-methylbutanoate (Int 6)

A mixture of benzaldehyde (2.9 mL, 28 mmol), Int 5 (5.9 g, 42 mmol), molecular sieves (5 g), and triethylamine (6.0 mL, 42 mmol) was stirred at ambient temperature for 6 hrs.

LCMS (Method B): 1.53 min, 208 [M+H]+
1H NMR (500 MHz, CDCl₃) δ 7.37-7.28 (m, 4H), 7.27-7.21 (m, 1H), 3.73 (s, 3H), 3.71 (s, 1H), 3.62 (d, 1H), 3.48 (q, 1H), 2.29 (s, 3H), 1.34 (d, 3H).
Preparation of (2S)-2-[benzyl(methyl)amino]propan-1-ol (Int 8)

To an ice cooled solution of Int 7 (1.3 g, 5.9 mmol) in anhydrous THF (12 mL) was added dropwise LiAlH₄ (1M solution in THF; 12 mL, 12 mmol) and the mixture was stirred in an ice bath for 2 hrs. The mixture was diluted with diethyl ether and quenched by sequential addition of water (0.45 mL) followed by 2M aqueous NaOH (0.45 mL) and water (1.5 mL). The phases were separated and the organic phase was dried over MgSO₄, filtered and concentrated in vacuo to give the title compound as a colourless oil (1.0 g). The crude product was used without further purification in subsequent reactions.

LCMS (Method B): 1.37 min, 180 [M+H]+

1H NMR (500 MHz, CDCl$_3$) δ 7.35-7.28 (m, 4H), 7.28-7.23 (m, 1H), 3.68 (d, 1H), 3.46 (d, 1H), 3.44-3.35 (m, 2H), 2.98 (dt, 1H), 2.15 (s, 3H), 0.93 (d, 3H).

Preparation of tert-butyl N—[(2S)-2-[benzyl(methyl)amino]propyl]carbamate (Int 9)

A mixture of Int 8 (0.61 g, 3.1 mmol), ethyl 2-{[(tert-butoxy)carbonyl]amino}-2-oxoacetate (630 μl, 3.1 mmol) and triphenylphosphine (0.88 g, 3.4 mmol) in anhydrous THF (20 mL) was cooled to −10° C. and treated with DEAD (0.48 mL, 3.1 mmol) by dropwise addition. The mixture was stirred at ambient temperature overnight. The solvent was removed in vacuo. The residue was poured onto brine/water (1:1, 20 mL) and extracted with diethyl ether. The combined organic phases were concentrated in vacuo. The residue was dissolved in THF (10 mL), LiOH (0.32 g, 13 mmol) and water (10 mL) were added and the mixture was stirred at ambient temperature for 2 hrs. The solvent was removed in vacuo. The residue was poured onto water (50 mL) and extracted with diethyl ether. The combined organic phases were concentrated in vacuo. The crude product was purified by chromatography on the Biotage Isolera Four™ (25 g column, 0 to 100% EtOAc in heptane) to afford title compound as a colourless oil (0.57 g).

LCMS (Method B): 1.88 min, 279 [M+H]$^+$

1H NMR (500 MHz, CDCl$_3$) δ 7.31 (d, 4H), 7.26-7.22 (m, 1H), 3.62 (d, 1H), 3.43 (d, 1H), 3.27-3.17 (m, 1H), 3.01-2.93 (m, 1H), 2.89-2.80 (m, 1H), 2.13 (s, 3H), 1.45 (s, 9H), 0.97 (d, 3H).

Preparation of tert-butyl N—[(2S)-2-(methylamino)propyl]carbamate (Int 10)

A solution of Int 9 (0.57 g, 1.6 mmol) in methanol (40 mL) was passed twice over a Pearlman's catalyst cartridge on the H-Cube® system (flow-rate of 1 mL/min, at 20 bar hydrogen pressure, at ambient temperature). The mixture was concentrated in vacuo to afford the title compound as a colourless oil (0.4 g). The crude product was used without further purification in subsequent reactions.

1H NMR (500 MHz, CDCl$_3$) δ 3.72 (d, 1H), 3.47 (d, 1H), 3.45 (s, 3H), 3.33-3.25 (m, 1H), 1.42 (s, 9H), 1.38 (d, 3H).

Preparation of N—[(2S)-1-aminopropan-2-yl]—N,6-dimethyl-3-(2H—1,2,3-triazol-2-yl)pyridine-2-carboxamide (Int 11)

To a solution of Int 10 (0.40 g, 1.6 mmol), Int 4 (0.39 g, 1.9 mmol) and DIPEA (0.83 mL, 4.8 mmol) in anhydrous DMF (7 mL) was added HATU (0.73 g, 1.9 mmol) and the mixture was stirred at ambient temperature for 16 hrs. The mixture was poured onto water (30 mL) and extracted with EtOAc. The combined organic phases were dried over MgSO$_4$, filtered and concentrated in vacuo. The crude intermediate was purified by chromatography on the Biotage Isolera Four™ (25 g column, 0 to 100% EtOAc in heptane). The resulting intermediate was dissolved in HCl (4M in dioxane; 10 mL, 40 mmol) and stirred at ambient temperature for 1 hr. The solvent was removed in vacuo. 2M Aqueous sodium hydroxide was added and the mixture extracted with EtOAc. The combined organic phases were dried over MgSO$_4$, filtered and concentrated in vacuo to afford the title compound as a yellow glass (0.37 g). The crude product was used without further purification in subsequent reactions.

LCMS (Method B): 1.19 min, 275 [M+H]$^+$

1H NMR (500 MHz, d6-DMSO) δ 8.24 (dd, 1H), 8.12 (d, 2H), 7.54-7.51 (m, 1H), 3.68-3.61 (m, 1H), 2.82 (s, 1H), 2.69 (s, 6H), 2.65 (s, 1H), 2.56 (d, 3H).

Preparation of N,6-dimethyl-3-(2H—1,2,3-triazol-2-yl)—N—[(2S)—1-{[5-(trifluoromethyl)pyrazin-2-yl]amino}propan-2-yl]pyridine-2-carboxamide (Example 1, Scheme 3)

Scheme 3

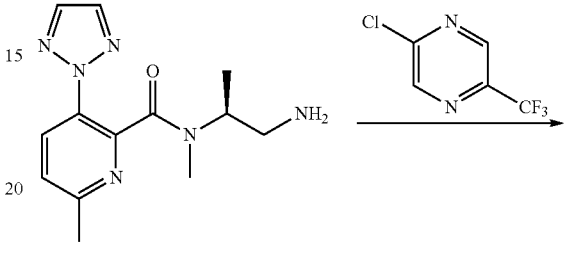

Int 11

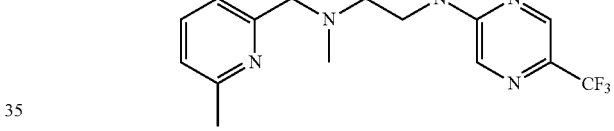

Example 1

To a stirred solution of Int 11 (0.58 g, 2.1 mmol) in THF (2 mL) was added DIPEA (1.0 mL, 5.8 mmol) followed by 2-chloro-5-(trifluoromethyl)pyrazine (0.39 g, 2.1 mmol) and the mixture was heated at 70° C. for 4 hrs. The reaction mixture was allowed to cool to ambient temperature and allowed to stand over the weekend. The reaction mixture was heated at 70° C. for a further 4 hrs with stirring and allowed to cool to ambient temperature. The reaction mixture was evaporated in vacuo. The residue was purified by preparative HPLC (Column: Waters Xbridge C18 (10 μm, 30×100 mm). Conditions: Water+0.2% ammonium hydroxide [Eluent A]; MeCN+0.2% ammonium hydroxide [Eluent B]. Gradient: 10 to 95% B) and then lyophilised to give title compound as a white solid (0.32 g)

LCMS (Method C): Two peaks at 4.20 and 4.39 min, 421 [M+H]$^+$

1H NMR (500 MHz, d4-MeOH) δ 8.38 (d, 0.15H), 8.34 (bs, 0.15H), 8.24 (d, 0.85H), 8.03 (bs, 0.85H), 7.99 (s, 0.30H), 7.97 (s, 1.70H), 7.85 (bs, 1.00H), 7.57 (d, 0.15H), 7.41 (d, 0.85H), 4.98 (m, 0.15H), 4.06 (bm, 0.85H), 3.50 (d, 0.15H), 3.47 (d, 0.85H), 3.42 (d, 0.85H), 3.39 (d, 0.15H), 3.05 (s, 2.55H), 2.83 (s, 0.45H), 2.65 (s, 0.45H), 2.45 (bs, 2.55H), 1.38 (d, 0.45H), 1.07 (bs, 2.55H).

Preparation of N,6-dimethyl-3-(2H—1,2,3-triazol-2-yl)—N—[(2S)—1-{[5-(trifluoro methyl)pyrimidin-2-yl]amino}propan-2-yl]pyridine-2-carboxamide (Example 2, Scheme 4)

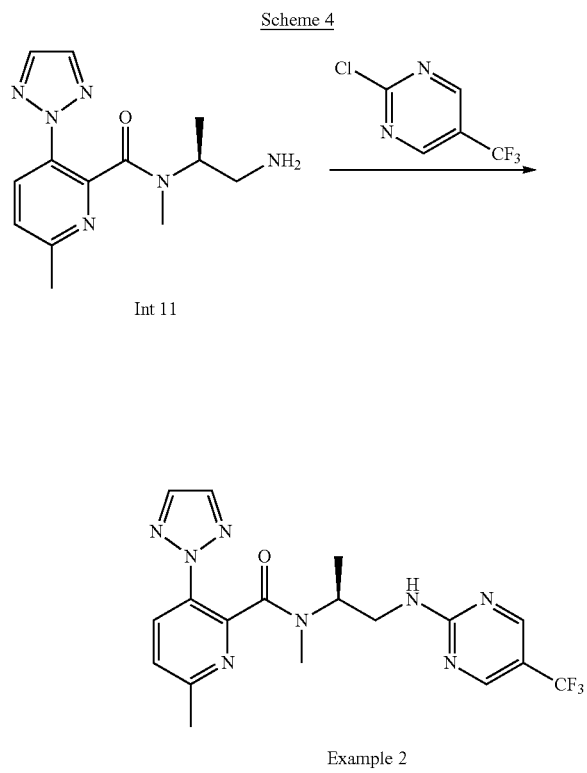

To a stirred suspension of Int 11 (0.72 g, 2.5 mmol) in THF (10 mL) was added 2-chloro-5-(trifluoromethyl)pyrimidine (0.69 g, 3.8 mmol) followed by DIPEA (860 μl, 5.1 mmol).

The reaction mixture was stirred for 2 hrs at ambient temperature and then at 30° C. for a further 3 hrs and then concentrated in vacuo. The crude product was dissolved in DMSO (9 mL) and purified by preparative HPLC (Column: Waters Sunfire C18 (10 μm, 30×100 mm). Conditions: Water+0.1% formic acid [Eluent A]; MeCN+0.1% formic acid [Eluent B]. Gradient: 10 to 95% B). The product was lyophilised from water (10 mL) and acetonitrile (2 mL) to give the title product as a white solid (0.51 g). EtOAc (2 mL) was added to the solid and heated at 80° C. with stirring. Heptanes (6 mL) was added slowly to this refluxing solution and allowed to cool to ambient temperature with stirring over 2 hrs. The white solid was filtered and washed with a 20% solution of EtOAc in heptane (2 mL) and dried to give the title compound as a white solid (0.42 g).

LCMS (Method C): Two peaks at 3.07 and 3.18 min, 421 [M+H]+

1H NMR (500 MHz, CDCl3) δ 8.50 (bd, 0.60H), 8.46 (s, 1.40H), 8.26 (d, 0.30H), 8.17 (d, 0.70H), 8.07 (s, 1.00H), 7.93 (bs, 1.40H), 7.87 (bs, 0.60H), 7.32 (d, 0.70H), 7.30 (d, 0.30H), 5.11 (bm, 0.30H), 4.13 (m, 0.70H), 3.82 (m, 0.30H), 3.64 (m, 0.70H), 3.54 (m, 0.30H), 3.29 (dt, 0.70H), 2.98 (s, 2.10H), 2.80 (s, 0.90H), 2.66 (s, 2.10H), 2.61 (s, 0.90H), 1.36 (m, 3.00H).

Alternative Methods for the Preparation of Example 1

Preparation of (2S)—N²—methyl—N¹—(5-(trifluoromethyl)pyrazin-2-yl)propane-1,2-diamine 1,3,5-Benzenetricarboxylic acid salt (Int 15, Scheme 5)

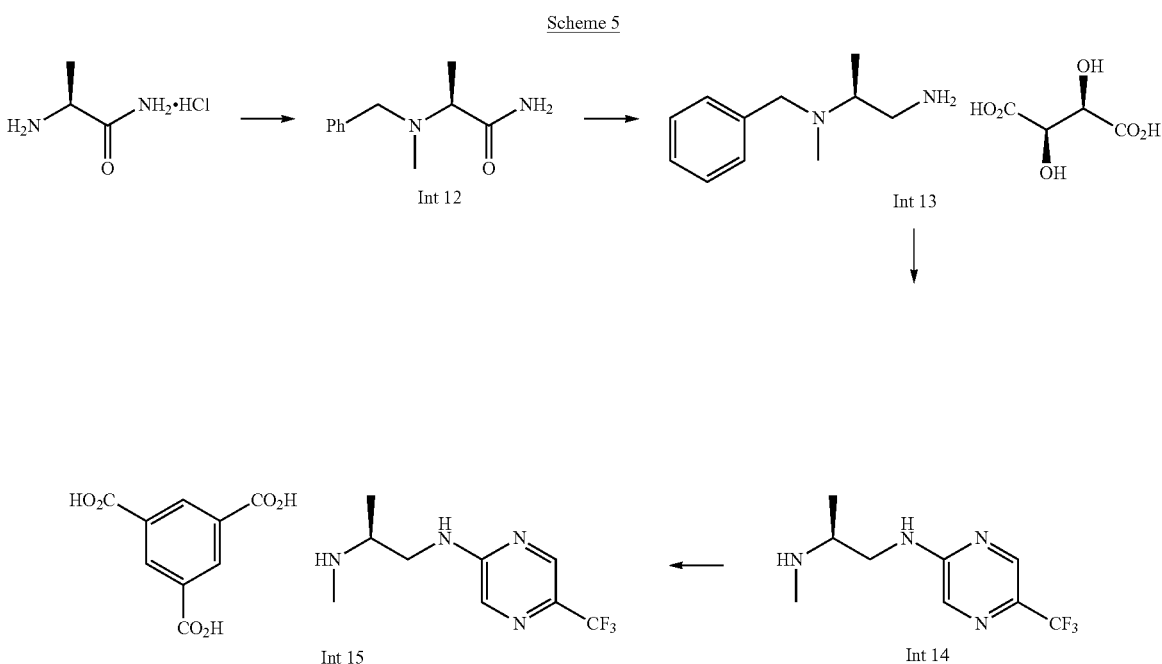

Preparation of (2S)-2-(benzyl(methyl)amino)propanamide (Int 12)

To a stirred suspension of (S)-2-aminopropanamide hydrochloride (1000 g, 8028 mmol) in ethanol (7000 mL) was added sodium hydroxide (321 g, 8028 mmol) followed by water (2000 mL) and benzaldehyde (854 mL, 8429 mmol). 5% Palladium on carbon (J-M Type 58, 150 g) was added as a slurry in ethanol (500 mL) and washed in with additional ethanol (500 mL). The mixture was vigorously agitated under an atmosphere of hydrogen at 3-3.5 bar pressure for 24 hrs. Paraformaldehyde (603 g, 2014 mmol) was added followed by 5% Palladium on carbon (J-M Type 58, 50 g) and the mixture vigorously agitated under an atmosphere of hydrogen at 3-3.5 bar pressure for 17 hrs. The reaction mixture was filtered through a pad of celite and washed with ethanol (2×2000 mL). The filtrate was concentrated to an approximate volume of 2000 mL and the concentrated solution partitioned between water (20000 mL) and tBME (20000 mL). The organic phase was collected and the aqueous extracted with further tBME (10000 mL). The organics were combined, concentrated to a volume of approximately 3000 mL and treated with heptane (12000 mL). The mixture was heated to 70° C. and tBME (2000 mL) added portion wise until the solution became clear. The solution was cooled and allowed to stand at 0-5° C. for 20 hrs. The resulting solid was collected by filtration and washed with cold heptane (5000 mL) to afford the title compound (835 g).

1H NMR (400 MHz, MeOD) δ 7.35-7.31 (m, 4H), 7.27-7.23 (m, 1H), 3.60 (s, 2H), 3.24 (q, 1H), 2.20 (s, 3H), 1.27 (d, 3H).

Preparation of (2S)—N²—benzyl—N²—methylpropane-1,2-diamine D-Tartaric acid salt (Int 13)

To a stirred solution of Int 12 (800 g, 4161 mmol) in anhydrous THF (6400 mL) under nitrogen at 0° C., was added LiAlH₄ (1 M in THF; 6242 mL, 6242 mmol) maintaining the reaction mixture at a temperature below 15° C. during the addition. The reaction mixture was warmed to 30° C. and stirred for 24 hrs before being cooled to 0° C. Water (224 mL), followed by a 15% solution of sodium hydroxide in water (224 mL) and then water (672 mL) were added cautiously, maintaining the reaction mixture at a temperature below 15° C. The reaction mixture was warmed to ambient temperature and tBME (2000 mL) was added and, after stirring for 1 hr, the mixture was filtered through a pad of celite washing with THF (2×1600 mL). The filtrate was concentrated to a volume of approximately 2400 mL and then THF (13600 mL) was added. The mixture was heated to 55° C. and a solution of D-tartaric acid (625 g, 4100 mmol) in methanol (2000 mL) added. The resulting suspension was stirred at 60-65° C. for 3 hrs, then cooled to ambient temperature and stirred for a further 10 hrs. The resulting solid was collected by filtration and washed with THF (2×6400 mL) to afford the title compound as a solid (1068 g).

1H NMR (500 MHz, d6-DMSO) δ 7.39 (d, 2H), 7.33 (t, 2H), 7.24 (t, 1H), 3.88 (s, 2H), 3.60 (d, 1H), 3.48 (d, 1H), 3.02-2.98 (m, 1H), 2.90-2.85 (m, 1H), 2.78-2.75 (m, 1H), 2.01 (s, 3H), 0.95 (d, 3H).

Preparation of (2S)—N²—methyl—N¹—(5-(trifluoromethyl)pyrazin-2-yl)propane-1,2-diamine (Int 14)

To a stirred mixture of tBME (6000 mL) and water (7000 mL) containing potassium carbonate (1326 g, 9593 mmol) was added Int 13 (1050 g, 3198 mmol) and water (1400 mL) followed by 2-chloro-5-(trifluoromethyl)pyrazine (584 g, 3198 mmol) and tBME (2400 mL). The mixture was heated to 50° C. and stirred vigorously for 24 hrs then cooled to ambient temperature. The organic phase was separated and washed with water (4200 mL). Ethanol (3000 mL) was added to the organics and the solution concentrated to a volume of approximately 3000 mL. This process was repeated twice more with ethanol (2100 mL and 5200 mL) and the resulting concentrated solution was treated with 10% Palladium on carbon (J-M Type 487, 260 g) as a slurry in ethanol (1000 mL) which was washed in with further ethanol (6500 mL). The mixture was stirred vigorously under an atmosphere of hydrogen at 3-3.5 bar pressure and at a temperature of 40° C. for 16 hrs. The solution was then cooled to ambient temperature and filtered through a pad of celite washing with ethanol (2100 mL) and the filtrate concentrated to dryness to afford the title compound as an oil (684 g).

1H NMR (400 MHz, MeOD) δ 8.29 (s, 1H), 7.97 (s, 1H), 3.52 (dd, 1H), 3.43 (dd, 1H), 2.96-2.90 (m, 1H), 2.44 (s, 3H), 1.16 (d, 3H).

Preparation of (2S)—N²—methyl—N¹—(5-(trifluoromethyppyrazin-2-yl)propane-1,2-diamine 1,3,5-Benzenetricarboxylic acid salt (Int 15)

To a stirred solution of benzene-1,3,5-tricarboxylic acid (71 g, 342 mmol) in ethanol (1600 mL) at 50° C. was added a solution of Int 14 (80 g, 342 mmol) in ethanol (800 mL). The resulting solution was warmed to 65-70° C. then stirred at this temperature for 3 hrs and at ambient temperature for 16 hrs. The mixture was concentrated to a volume of approximately 800 mL, tBME (2000 mL) added and the resulting suspension stirred vigorously for 16 hrs. The solid was collected by filtration and washed with tBME (2×800 mL) to afford the title compound as a solid (123 g).

1H NMR (400 MHz, MeOD) δ 8.78 (s, 3H), 8.34 (s, 1H), 8.05 (s, 1H), 3.81 (dd, 1H), 3.69 (dd, 1H), 3.57-3.49 (m, 1H), 2.76 (s, 3H), 1.39 (d, 3H).

Preparation of (2S)—N²—methyl—N¹—(5-(trifluoromethyppyrazin-2-yl)propane-1,2-diamine (Int 14, Scheme 6)

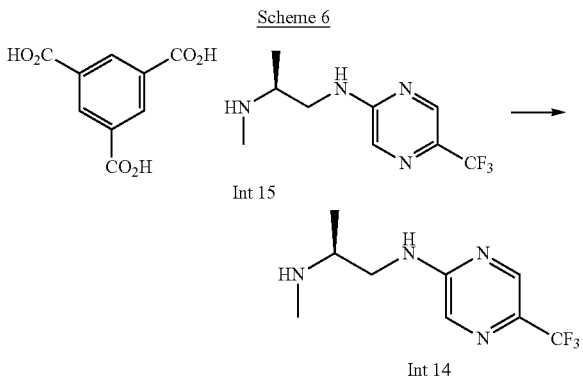

Scheme 6

To a white stirred suspension of Int 15 (10.6 g, 23.8 mmol) in EtOAc (50 mL) was added a solution of potassium carbonate (9.9 g, 71 mmol) in water (75 mL). The resulting bi-phasic mixture was stirred vigorously at ambient temperature for 3 hrs. The organic phase was collected and the aqueous washed with EtOAc (2×50 mL). The combined organic extracts were concentrated to dryness to afford the title compound as an oil (4.69 g).

Preparation of 2-methyl-5-(2H—1,2,3-triazol-2-yl)pyridine (Int 1, Scheme 1)

Int 1 may be prepared by the method described in Scheme 1 but with 0.5 equivalents of copper powder.

Int 1 may be prepared using the method described in Scheme 1 but with 2 equivalents of potassium carbonate. Preparation of N,6-dimethyl-3-(2H—1,2,3-triazol-2-yl)—N—[(2S)—1-{[5-(trifluoro methyl)pyrazin-2-yl]amino}propan-2-yl]pyridine-2-carboxamide (Example 1, Scheme 7)

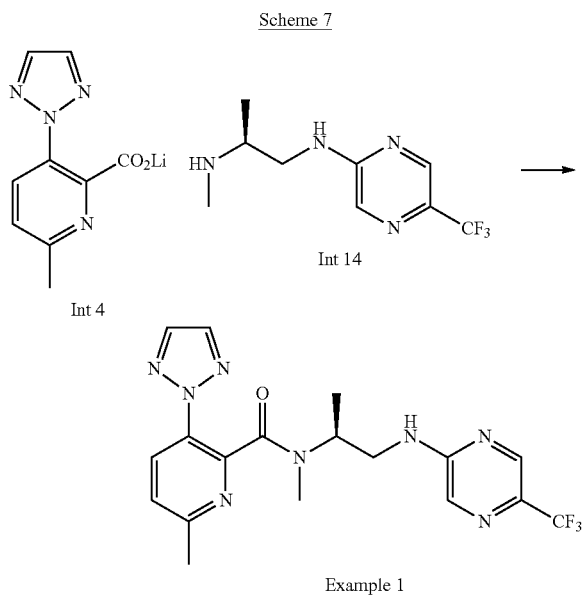

Scheme 7

Example 1

To a stirred suspension of Int 4 (420 g, 1999 mmol) in EtOAc (4200 mL) under a nitrogen atmosphere was added thionyl chloride (438 mL, 5997 mmol) over 5 mins. The temperature of the reaction was increased to 65° C. and the mixture stirred for 3 hrs at this temperature. Additional thionyl chloride (73 mL, 999 mmol) was added and stirring continued for 1 hr. Further thionyl chloride was added (73 mL, 1000 mmol) and the reaction stirred at 70° C. for 1 hr and then at ambient temperature for 16 hrs. The reaction mixture was concentrated to dryness, EtOAc (4200 mL) added and the process repeated. The residue was treated with EtOAc (8000 mL) and cooled to 0-5° C. under nitrogen. A solution of triethylamine (557 mL, 3998 mmol) in EtOAc (800 mL) was added dropwise followed by the portion-wise addition of a solution of Int 14 (468 g, 1999 mmol) in EtOAc (3200 mL) maintaining the reaction temperature at 0° C. The reaction was warmed to ambient temperature and stirred for 16 hrs. Water (6300 mL) was added and the bi-phasic mixture filtered through a pad of Celite. The organic phase was collected, washed with a saturated aqueous solution of NaHCO$_3$ (6300 mL) and water (3000 mL). Charcoal (43 g) was added to the organic extracts and the resulting black suspension stirred for 24 hours at 50° C. The charcoal was removed by filtration through a pad of Celite and the filtrate concentrated to an approximate volume of 2100 mL. The concentrated solution was treated with EtOAc (2100 mL), water (1100 mL) and heptane (11000 mL) and the resulting suspension heated to 70° C. Further EtOAc (1600 mL) was added until full dissolution was achieved. The reaction was allowed to cool to ambient temperature and stirred for 16 hrs. The resulting precipitate was collected by filtration, washed twice with heptane (4200 mL) and dried to afford the title compound as a solid (480 g).

Biological Assays

Antagonism against orexin receptors has been measured for each example compound using at least one of the following procedures. Antagonism is reported as a pIC$_{50}$, where pIC$_{50}$=−log$_{10}$(IC$_{50}$) and where IC$_{50}$ is the concentration of example compound needed to inhibit 50% of the agonist response. These values may fluctuate depending on the daily cellular assay performance. Fluctuations of this kind are known to those skilled in the art. All reported values are the result of at least four replicate experiments. Ox2 values are only reported from dose response curves for which the top concentration is at least 10 μM.

Ox1 and Ox2 Antagonist FLIPR assay:

Test compounds are prepared as 20 mM stock solutions in DMSO, then serially diluted in half log concentrations with DMSO followed by dilution with assay buffer (HBSS Gibco, 14065-049) containing 20 mM HEPES (Gibco, 15630-56), 2.5 mM Probenecid; 0.1% (w/v) pluronic F127 (Sigma, P2443) and adjusted to pH 7.4) to a top final assay concentration of 1 μM or 10 μM, depending on the potency at a given human OX receptor.

Human OX$_1$ or human OX$_2$ receptor expressing CHO cells are plated into 384 well black, clear bottom, CellBIND plates at a seeding density of 10,000 cells/75 μL growth media. The seeded plates are incubated at 37° C. in air supplemented with 5% CO$_2$ overnight.

The next day media is removed and replaced with 30 μL/well of cell loading buffer (a vial of Calcium 5 is solubilized in 20 mL of assay buffer) and the cells incubated for 1 hr at 37° C. The serially diluted test compounds (10 μL/well) are added to the cell plate by the FLIPR Tetra and the addition is monitored for 5 min by the instrument. The cell plate is then removed and incubated for additional 25 min in a humidified incubator at 37° C. prior to being placed back into the FLIPR Tetra. Finally 10 μL of orexin A in assay buffer+0.1% (w/v) bovine serum albumin is dispensed by the FLIPR Tetra at an EC75 concentration determined for each receptor on the day of the assay. Fluorescence is measured at excitation and emission wavelengths of 485 nm and 525 nm, respectively and data analyzed using Graph Pad Prism for the EC$_{75}$ value of orexin A and Aplus to determine a PIC$_{50}$ value for each test compound. Established QC criteria (z'value and potency of pharmacological reference compounds) are applied to declare a plate as failed or approved for database upload.

All reported values are the result of at least four replicates.

Ox2 values are only reported from dose response curves for which the top concentration is at least 10 μM.

Orexin 1 Receptor Radioligand Binding Assay:

Cell membranes were prepared from the human OX$_1$ receptor expressing CHO cell line. The harvested cell pellets were homogenized in ice-cold buffer (15 mM TrisHCl (pH 7.5), 2 mM MgCl$_2$, 0.3 mM EDTA, 1 mM EGTA, Sigma protease inhibitor cocktail) and centrifuged at 41,000 g for 20 min at 4° C. After discarding the supernatants the pellets were re-suspended in the before mentioned buffer followed by homogenization and another centrifugation. Obtained pellets were re-suspended in ice cold buffer containing 75 mM TrisHCl (pH 7.5), 12.5 mM MgCl$_2$, 0.3 mM EDTA, 1 mM EGTA, 250 mM sucrose and a protease inhibitor cocktail (Sigma). After protein quantification with the Pierce Protein Assay Kit, using BSA as standard, the membrane homogenates were aliquoted and frozen down at 80° C. until further use.

Expression levels of the Ox1 receptor (Bmax) were determined by saturation binding and the Kd of the radioligand [$^3$H]SB674042 was determined by association and dissociation kinetics. Data were elaborated with Graph Pad Prism using radioligand binding analysis. Steady state binding was reached after 90 min of incubation at room temperature.

In competition binding experiments, 1 nM of [3H]-SB674042 was incubated at room temperature for 90 min with 1.5 µg membrane protein and increasing concentrations of displacing compounds in binding buffer (25 mM HEPES pH7.3, 1 mM CaCl2, 5 mM MgCl2, 0.1% (w/v) BSA and 0.02% (w/v) pluronic acid) in a total assay volume of 200 µl. Reactions were stopped by rapid filtration onto GF/B filters that have been pre-soaked with 0.5% PEI. After filter drying, 30 µl/well of Microscint 0 are added, and the radioactivity measured on a Microbeta counter (Perkin-Elmer). Data were elaborated using Graph Pad Prism. The 50% inhibitory concentration (IC50) obtained in competition binding experiments, using non-linear regression fitted to one-site model analysis was converted to Ki by the Cheng-Prusoff equation, Ki=IC50/[1+([L]/Kd)], where [L] is the ligand concentration and Kd the equilibrium dissociation constant (Cheng and Prusoff, 1973).

Orexin 2 Receptor Radioligand Binding Assay:

Cell membranes were prepared from the human Ox2 receptor expressing CHO cell line. The harvested cell pellets were homogenized in ice-cold buffer (15 mM TrisHCl (pH 7.4), 2 mM $MgCl_2$, 0.3 mM EDTA, 1 mM EGTA, Sigma FAST™ protease inhibitor cocktail) and centrifuged at 45,000 rpm for 30 min at 4° C. After discarding the supernatants the pellets were re-suspended in the before mentioned buffer followed by homogenization and another centrifugation. Obtained pellets were re-suspended in ice cold buffer containing 75 mM TrisHCl (pH 7.5), 12.5 mM $MgCl_2$, 0.3 mM EDTA, 1 mM EGTA, 250 mM sucrose and a Sigma FAST TM protease inhibitor cocktail. After protein quantification with the Pierce Protein Assay Kit, using BSA as standard, the membrane homogenates were aliquoted and frozen down at 80° C. until further use.

Expression levels of the Ox2 receptor (Bmax) were determined by saturation binding and the Kd of the radioligand [³H]EMPA was determined by association and dissociation kinetics. Data were elaborated with Graph Pad Prism using radioligand binding analysis. Steady state binding was reached after 60 min of incubation at room temperature.

In competition binding experiments, 2 nM of [3H]-EMPA was incubated at room temperature for 60 min with 4 µg membrane protein and increasing concentrations of displacing compounds in binding buffer (25 mM HEPES pH7.4, 1 mM CaCl2, 5 mM MgCl2, 0.5% (w/v) BSA and 0.05% (w/v) pluronic acid) in a total assay volume of 200 µl. Reactions were stopped by rapid filtration onto GF/B filters that have been pre-soaked with 0.5% PEI. After filter drying, 30 µl/well of Microscint 0 are added, and the radioactivity measured on a Microbeta counter (Perkin-Elmer). Data were elaborated using Graph Pad Prism. The 50% inhibitory concentration (IC50) obtained in competition binding experiments, using non-linear regression fitted to one-site model analysis was converted to Ki by the Cheng-Prusoff equation, Ki=IC50/[1+([L]/Kd)], where [L] is the ligand concentration and Kd the equilibrium dissociation constant (Cheng and Prusoff, 1973).

|  | Example 1 | Example 2 |
|---|---|---|
| hOX1 $pIC_{50}$ | 9.1 | 8.9 |
| hOX2 $pIC_{50}$ | 6.0 | 5.7 |
| hOX1 pKi | 9.0 | 8.8 |
| hOX2 pKi | 6.6 | 6.1 |

Kinetics of competitive binding (Motulski and Mahan's analysis):

Motulsky and Mahan characterisation of the Examples was performed as described by Faedo et al., *European Journal of Pharmacology* 692(2012), p.1-9 with the following modifications:

The association binding experiment was initiated by addition of membranes expressing the human Orexin 1 receptor at different times to the incubation buffer containing 1 nM of [³H] SB674042. Non-specific binding was determined in the presence of 10 µM of SB674042. The association of the radioligand to the orexin receptor was performed as described for the kinetics experiment in the presence of the competing test compounds. The competing test compounds were assayed at three concentrations corresponding to 3, 10 and 30 fold of the determined Ki. For kinetic binding studies of the human Orexin 2 receptor, the method described for the Orexin 1 receptor was used with modifications that membranes expressing the human Orexin 2 receptor were incubated in buffer containing 1 nM of [3H] EMPA and non-specific binding was determined in the presence of 10 µM ACT-078573.

Orexin 1 Receptor Results

|  | pKi (M&M) | $K_{on}$ (M − 1 min − 1) | $K_{off}$ (min − 1) | $T_{1/2}$ (min) | tR (min) |
|---|---|---|---|---|---|
| Example 1[a] | 9.5 | 7.82E+06 | 0.003 | 248 | 357 |
| Example 1[b] | 9.1 | 8.77E+06 | 0.007 | 104 | 150 |
| Example 1[c] | 9.3 | 8.39E+06 | 0.005 | 170 | 245 |
| Example 2[a] | 8.6 | 4.52E+06 | 0.010 | 67 | 96 |
| Example 2[d] | 8.6 | 4.68E+06 | 0.011 | 60 | 87 |
| Example 2[e] | 8.6 | 4.57E+06 | 0.011 | 65 | 93 |

[a]Mean obtained from initial results using the compound of Example 1 and Example 2 (n = 2)
[b]Mean obtained from further test results obtained using the compound of Example 1 (n = 3)
[c]Mean of all results obtained using the compound of Example 1 (n = 5)
[d]Further test result obtained using the compound of Example 2 (n = 1)
[e]Mean of all results obtained using the compound of Example 2 (n = 3)

Orexin 2 Receptor Results:

|  | pKi (M&M) | $K_{on}$ (M − 1 min − 1) | $K_{off}$ (min − 1) | $T_{1/2}$ (min) | tR (min) |
|---|---|---|---|---|---|
| Example 1 | 6.5 | 6.46E+05 | 0.211 | 4.1 | 5.9 |
| Example 2 | 5.8 | 1.10E+05 | 0.179 | 4.3 | 6.2 |

The results for the Orexin-2 Receptor studies are the mean of the results from 3 studies (n=3) for both Example compounds.

REFERENCES

1. De Lecea, L. (1998). The hypocretins: Hypothalamus-specific peptides with neuroexcitatory activity. *Proceedings of the National Academy of Sciences*, 95(1), 322-327. doi: 10.1073/pnas.95.1.322
2. Sakurai, T., Amemiya, A., Ishii, M., Matsuzaki, I., Chemelli, R. M., Tanaka, H., Williams, S. C., et al. (1998).

Orexins and orexin receptors: a family of hypothalamic neuropeptides and G protein-coupled receptors that regulate feeding behavior. *Cell*, 92(4), 573-85. Retrieved from http://www.ncbi.nlm.nih.gov/pubmed/9491897

3. Lee, J. H., Bang, E., Chae, K. J., Kim, J. Y., Lee, D. W., & Lee, W. (1999). Solution structure of a new hypothalamic neuropeptide, human hypocretin-2/orexin-B. *European Journal of Biochemistry*, 266(3), 831-839. doi:10.1046/j.1432-1327.1999.00911.x 4. Peyron, C., Tighe, D. K., Van den Pol, A. N., De Lecea, L., Heller, H. C., Sutcliffe, J. G., & Kilduff, T. S. (1998). Neurons Containing Hypocretin (Orexin) Project to Multiple Neuronal Systems. *J. Neurosci.*, 18(23), 9996-10015. Retrieved from http://www.jneurosci.org/content/18/23/9996.long 5. Van den Pol, A. N., Gao, X. B., Obrietan, K., Kilduff, T. S., & Belousov, A. B. (1998). Presynaptic and Postsynaptic Actions and Modulation of Neuroendocrine Neurons by a New Hypothalamic Peptide, Hypocretin/Orexin. *J. Neurosci.*, 18(19), 7962-7971. Retrieved from http://www.jneurosci.org/content/18/19/7962.long 6. Boss, C., Brisbare-Roch, C., & Jenck, F. (2009). Biomedical application of orexin/hypocretin receptor ligands in neuroscience. *Journal of Medicinal Chemistry*, 52(4), 891-903. doi:10.1021/jm801296d 7. Brisbare-Roch, C., Dingemanse, J., Koberstein, R., Hoever, P., Aissaoui, H., Flores, S., Mueller, C., et al. (2007). Promotion of sleep by targeting the orexin system in rats, dogs and humans. *Nature Medicine*, 13(2), 150-5. doi:10.1038/nm1544

8. Urbańska, A., Sokołowska, P., Woldan-Tambor, A., Biegańska, K., Brix, B., Jöhren, O., Namiecińska, M., et al. (2012). Orexins/hypocretins acting at Gi protein-coupled OX 2 receptors inhibit cyclic AMP synthesis in the primary neuronal cultures. *Journal of Molecular Neuroscience: MN*, 46(1), 10-7. doi:10.1007/s12031-011-9526-2

9. Matsuki, T., & Sakurai, T. (2008). Orexins and orexin receptors: from molecules to integrative physiology. *Results and Problems in Cell Differentiation*, 46, 27-55. doi:10.1007/400_2007_047

10. Chemelli, R. M., Willie, J. T., Sinton, C. M., Elmquist, J. K., Scammell, T., Lee, C., Richardson, J. A., et al. (1999). Narcolepsy in orexin Knockout MiceMolecular Genetics of Sleep Regulation. *Cell*, 98(4), 437-451. doi:10.1016/S0092-8674(00)81973-X 11. Mieda, M. (2002). Sleep, feeding, and neuropeptides: roles of orexins and orexin receptors. *Current Opinion in Neurobiology*, 12(3), 339-345. doi:10.1016/50959-4388(02)00331-8

12. Lin, L., Faraco, J., Li, R., Kadotani, H., Rogers, W., Lin, X., Qiu, X., et al. (1999). The Sleep Disorder Canine Narcolepsy Is Caused by a Mutation in the Hypocretin (Orexin) Receptor 2 Gene. *Cell*, 98(3), 365-376. doi:10.1016/50092-8674(00)81965-0

13. Nishino, S., Ripley, B., Overeem, S., Nevsimalova, S., Lammers, G. J., Vankova, J., Okun, M., et al. (2001). Low cerebrospinal fluid hypocretin (Orexin) and altered energy homeostasis in human narcolepsy. *Annals of Neurology*, 50(3), 381-8. Retrieved from http://www.ncbi.nlm.nih.gov/pubmed/11558795

14. Peyron, C., Faraco, J., Rogers, W., Ripley, B., Overeem, S., Charnay, Y., Nevsimalova, S., et al. (2000). A mutation in a case of early onset narcolepsy and a generalized absence of hypocretin peptides in human narcoleptic brains. *Nature Medicine*, 6(9), 991-7. doi:10.1038/79690

15. Gatfield, J., Brisbare-Roch, C., Jenck, F., & Boss, C. (2010). Orexin receptor antagonists: a new concept in CNS disorders? *ChemMedChem*, 5(8), 1197-214. doi:10.1002/cmdc.201000132

16. Herring, W. J., Snyder, E., Budd, K., Hutzelmann, J., Snavely, D., Liu, K., Lines, C., et al. (2012). Orexin receptor antagonism for treatment of insomnia: a randomized clinical trial of suvorexant. *Neurology*, 79(23), 2265-74. doi:10.1212/WNL.0b013e31827688ee 17. Willie, J. T., Chemelli, R. M., Sinton, C. M., Tokita, S., Williams, S. C., Kisanuki, Y. Y., Marcus, J. N., et al. (2003). Distinct Narcolepsy Syndromes in Orexin Receptor-2 and Orexin Null Mice. *Neuron*, 38(5), 715-730. doi:10.1016/50896-6273(03)00330-1

18. Hoever, P., Dorffner, G., Beneš, H., Penzel, T., Danker-Hopfe, H., Barbanoj, M. J., Pillar, G., et al. (2012). Orexin receptor antagonism, a new sleep-enabling paradigm: a proof-of-concept clinical trial. *Clinical Pharmacology and Therapeutics*, 91(6), 975-85. doi:10.1038/clpt.2011.370

19. Bernardis, L. L., & Bellinger, L. L. (1993). The lateral hypothalamic area revisited: Neuroanatomy, body weight regulation, neuroendocrinology and metabolism. *Neuroscience & Biobehavioral Reviews*, 17(2), 141-193. doi:10.1016/S0149-7634(05)80149-6

20. Haynes, A. C., Jackson, B., Overend, P., Buckingham, R. E., Wilson, S., Tadayyon, M., & Arch, J. R. (1999). Effects of single and chronic intracerebroventricular administration of the orexins on feeding in the rat. *Peptides*, 20(9), 1099-1105. doi:10.1016/S0196-9781(99)00105-9

21. Yamada, H., Okumura, T., Motomura, W., Kobayashi, Y., & Kohgo, Y. (2000). Inhibition of food intake by central injection of anti-orexin antibody in fasted rats. *Biochemical and Biophysical Research Communications*, 267(2), 527-31. doi:10.1006/bbrc.1999.1998

22. Rodgers, R. J., Halford, J. C. G., Nunes de Souza, R. L., Canto de Souza, A. L., Piper, D. C., Arch, J. R. S., Upton, N., et al. (2001). SB-334867, a selective orexin-1 receptor antagonist, enhances behavioural satiety and blocks the hyperphagic effect of orexin-A in rats. *European Journal of Neuroscience*, 13(7), 1444-1452. doi:10.1046/j.0953-816x.2001.01518.x 23. Piccoli, L., Vittoria, M., Di, M., Cifani, C., Costantini, V. J. A., Massagrande, M., Montanari, D., et al. (2012). Role of Orexin-1 Receptor Mechanisms on Compulsive Food Consumption in a Model of Binge Eating in Female Rats. *Neuropsychopharmacology*, 37(9), 1999-2011. doi:10.1038/npp.2012.48

24. López, M., Seoane, L., García, M. C., Lago, F., Casanueva, F. F., Señaris, R., & Diéguez, C. (2000). Leptin regulation of prepro-orexin and orexin receptor mRNA levels in the hypothalamus. *Biochemical and Biophysical Research Communications*, 269(1), 41-5. doi:10.1006/bbrc.2000.2245

25. Pizza, F., Magnani, M., Indrio, C., & Plazzi, G. (2013). The Hypocretin System and Psychiatric Disorders. *Current Psychiatry Reports*, 16(2), 433. doi:10.1007/s11920-013-0433-9

26. Von der Goltz, C., Koopmann, A., Dinter, C., Richter, A., Grosshans, M., Fink, T., . . . Kiefer, F. (2011). Involvement of orexin in the regulation of stress, depression and reward in alcohol dependence. *Hormones and Behavior*, 60(5), 644-50. doi:10.1016/j.yhbeh.2011.08.017

27. Johnson, P. L., Truitt, W., Fitz, S. D., Minick, P. E., Dietrich, A., Sanghani, S., . . . Shekhar, A. (2009). A key role for orexin in panic anxiety. *Nature Medicine*, 16(1), 111-115. doi:10.1038/nm.2075

28. Harris, G. C., Wimmer, M., & Aston-Jones, G. (2005). A role for lateral hypothalamic orexin neurons in reward seeking. *Nature,* 437(7058), 556-9. doi:10.1038/nature04071

29. Boutrel, B., Kenny, P. J., Specio, S. E., Martin-Fardon, R., Markou, A., Koob, G. F., & de Lecea, L. (2005). Role for hypocretin in mediating stress-induced reinstatement of cocaine-seeking behavior. *Proceedings of the National Academy of Sciences of the United States of America,* 102(52), 19168-73. doi:10.1073/pnas.0507480102

30. Lawrence, A. J., Cowen, M. S., Yang, H. J., Chen, F., & Oldfield, B. (2006). The orexin system regulates alcohol-seeking in rats. *British Journal of Pharmacology,* 148(6), 752-9. doi:10.1038/sj.bjp.0706789

31. Harris, G. C., & Aston-Jones, G. (2006). Arousal and reward: a dichotomy in orexin function. *Trends in Neurosciences,* 29(10), 571-7. doi:10.1016/j.tins.2006.08.002

32. Harris, G. C., Wimmer, M., & Aston-Jones, G. (2005). A role for lateral hypothalamic orexin neurons in reward seeking. *Nature,* 437(7058), 556-9. doi:10.1038/nature04071

33. Hollander, J. A., Lu, Q., Cameron, M. D., Kamenecka, T. M. & Kenny P. J. (2008). Insular hypocretin transmission regulates nicotine reward. *PNAS,* 105(49), 19480-19485.

34. LeSage, M. G., Perry, J. L., Kotz, C. M., Shelley, D. & Corrigall, W. A. (2010). Nicotine self-administration in the rat: effects of hypocretin antagonists and changes in hypocretin mRNA. *Psychopharmacology,* 209, 203-212.

35. Plaza-Zabala, A., Martin-García, E., de Lecea, L., Maldonado, R. & Berrendero, F. (2010). Hypocretins regulate the anxiogenic-like effects of nicotine and induce reinstatement of nicotine-seeking behaviour. *J Neurosci.,* 30(6), 2300-2310.

36. Plaza-Zabala, A., Martín-García, E., de Lecea, L., Maldonado, R. & Berrendero, F. (2013). A role for Hypocretin/Orexin Receptor-1 in Cue-Induced Reinstatement of Nicotine-seeking behaviour. *Neuropsychopharmacology,* 38, 1724-1736.

37. Swinney, D.C. (2009). The role of binding kinetics in therapeutically useful drug action. *Curr Opin Drug Discov Devel.* 12(1):31-9.

38. Tummino, P. J., Copeland, R. A. (2008). Residence time of receptor-ligand complexes and its effect on biological function. *Biochemistry.* 47(20):5481-92.

The invention claimed is:

1. A process for the preparation of a compound or formula I or a pharmaceutically acceptable salt or solvate thereof:

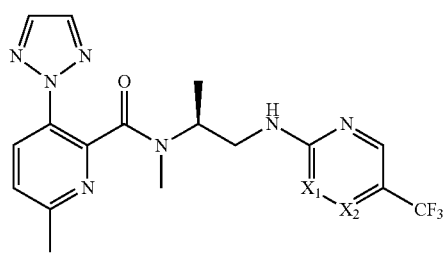

I wherein $X_1$ is —CH— and $X_2$ is —N—, or $X_1$ is —N— and $X_2$ is —CH;

the process comprising:

(A) the reaction of a compound of formula II or a salt thereof, with an amide coupling reagent and a compound of formula III or a salt thereof:

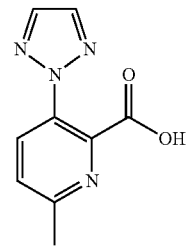

II

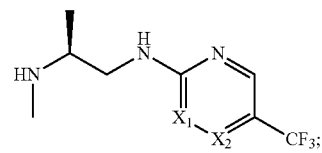

III and, if desired, the conversion of the compound of formula I to a salt or solvate thereof; or (B) the reaction of N—[(2S)-1-aminopropan-2-yl]—N,6-dimethyl-3-(2H—1,2,3-triazol-2-yl)pyridine-2-carboxamide:

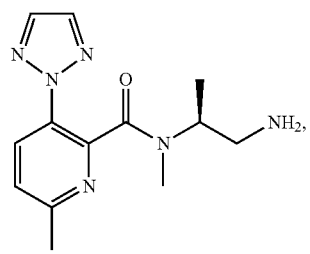 [SMILES: Cc1ccc(-n2nccn2)c(C(=O)N(C)[C@@H](C)CN)n1]

in the presence of a base with the following heteroaryl compound:

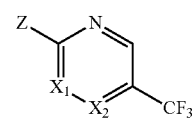

wherein Z is a leaving group selected from halide, tosylate and mesylate; and, if desired, the conversion of the compound of formula I to a salt or solvate thereof.

2. The process according to claim 1, wherein $X_1$ is —CH— and $X_2$ is —N—.

3. The process according to claim 1, wherein the salt of the compound of formula II is the lithium salt:

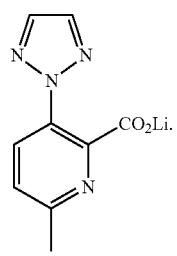

4. The process according to claim 1, wherein the amide coupling reagent is selected from thionyl chloride, isobutyl chloroformate, pentafluorophenyl trifluoracetate, N—hydroxybenzotriazole, dicyclohexylcarbodiimide and HATU.

5. The process according to claim 4, wherein the amide coupling reagent is thionyl chloride.

6. The process according to claim 1, wherein Z is chloride.

7. The process according to claim 1, wherein the base is a tertiary amine base, such as DIPEA.

* * * * *